US011484521B2

(12) United States Patent
Peterson et al.

(10) Patent No.: US 11,484,521 B2
(45) Date of Patent: Nov. 1, 2022

(54) ANTIDOTES TO CYANIDE POISONING

(71) Applicants: The General Hospital Corporation, Boston, MA (US); THE REGENTS OF THE UNIVERSITY OF CALIFORNIA, Oakland, CA (US)

(72) Inventors: Randall Peterson, Stoneham, MA (US); Robert Gerszten, Brookline, MA (US); Anjali Nath, Boston, MA (US); Calum MacRae, Wellesley Hills, MA (US); Gerry Boss, La Jolla, CA (US); Matt Brenner, Irvine, CA (US); Sari Brenner Mahon, Irvine, CA (US)

(73) Assignees: The General Hospital Corporation, Boston, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/604,510

(22) PCT Filed: Apr. 12, 2018

(86) PCT No.: PCT/US2018/027361
§ 371 (c)(1),
(2) Date: Oct. 10, 2019

(87) PCT Pub. No.: WO2018/191537
PCT Pub. Date: Oct. 18, 2018

(65) Prior Publication Data
US 2020/0276148 A1 Sep. 3, 2020

Related U.S. Application Data

(60) Provisional application No. 62/484,623, filed on Apr. 12, 2017.

(51) Int. Cl.
*A61K 31/282* (2006.01)
*A61P 39/02* (2006.01)
*A61K 9/00* (2006.01)

(52) U.S. Cl.
CPC ............ *A61K 31/282* (2013.01); *A61P 39/02* (2018.01); *A61K 9/0019* (2013.01)

(58) Field of Classification Search
CPC .............................. A61K 31/282; A61P 39/02
See application file for complete search history.

(56) References Cited

U.S. PATENT DOCUMENTS

| 5,674,904 | A | 10/1997 | Moore | |
|---|---|---|---|---|
| 2008/0254145 | A1* | 10/2008 | Colin | A61K 33/243 530/324 |
| 2011/0110850 | A1 | 5/2011 | Barnham et al. | |
| 2015/0297535 | A1 | 10/2015 | Petrikovics et al. | |

FOREIGN PATENT DOCUMENTS

| DE | 293496 | 9/1991 | |
|---|---|---|---|
| GB | 2304712 A | * 3/1997 | ........... C07D 471/04 |

OTHER PUBLICATIONS

Fischer et al., "Cisplatin and dimethyl sulfoxide react to form an adducted compound with reduced cytotoxicity and neurotoxicity," NeuroToxicology 29 (2008) 444-452.*
Zenda et al., "A Cisplatin Derivative that Inhibits Collagen Fibril-Formation in vitro," Chem Biol Drug Des 2015; 85: 519-526.*
Bogdanovic et al., Growth Effects of Some Platinum (Ii) Complexes with Sulfur-Containing Carrier Ligands on MCF7 Human Breast Cancer Cell Line upon Simultaneous Administration with Taxol, Metal-Based Drugs vol. 9, Nos. 1-2, 2002 (Year: 2002).*
Anderson et al., "Protection against cisplatin toxicity by administration of glutathione ester," FASEB J., Nov. 1990, 4(14):3251-3255.
Anseeuw et al., "Antidotes for cyanide poisoning," European Journal of Emergency Medicine, Jan. 2013, 20(1):66-67.
Antonini et al., "The interaction of cyanide with cytochrome oxidase," Eur. J. Biochem., 1971, 23(2):396-400.
Banerjea et al., "Mechanism of Substitution Reactions of Complex Ions. XII. Reactions of Some Platinum(II) Complexes with Various Reactants," Journal of the American Chemical Society, Aug. 1957, 79(15):4055-4062.
Barillo et al., "Cyanide poisoning in victims of fire: analysis of 364 cases and review of the literature," J. Burn Care Rehabil., Jan. 1994, 15(1):46-57.
Basolo & Pearson., "The Trans Effect in Metal Complexes," Progress in Inorganic Chemistry, 2007, 4:381-453.
Bebarta et al., "Intravenous cobinamide versus hydroxocobalamin for acute treatment of severe cyanide poisoning in a swine (Sus scrofa) model," Ann. Emerg. Med., Apr. 2014, 64(6):612-619.
Bebarta et al., "Sodium Nitrite and Sodium Thiosulfate Are Effective Against Acute Cyanide Poisoning When Administered by Intramuscular Injection," Ann. Emerg. Med., Jun. 2017, 69(6):718-725, e4.
Braddock et al., "Structure and activity relationships of platinum complexes with anti-tumour activity," Chem. Biol. Interact., 1975, 11(3):145-161.
Brenner et al., "Comparison of cobinamide to hydroxocobalamin in reversing cyanide physiologic effects in rabbits using diffuse optical spectroscopy monitoring," J. Biomed. Opt., Jan./Feb. 2010, 15(1):017001, 8 pages.
Brenner et al., "Intramuscular cobinamide sulfite in a rabbit model of sublethal cyanide toxicity," Ann. Emerg. Med., Apr. 2010, 55(4):352-363.
Broughton., "The Bhopal disaster and its aftermath: a review," Environ. Health, Dec. 2005, 4(1):6.
Chan et al., "Nitrocobinamide, a new cyanide antidote that can be admimstered by intramuscular injection," J. Med. Chem., Feb. 2015, 58(4)1750-1759.
Dalgaard, "Comparison of minipig, dog, monkey and human drug metabolism and disposition," J. Pharmacol. Toxicol. Methods, Jul./Aug. 2015, 74:80-92, Accepted Manuscript.

(Continued)

*Primary Examiner* — Jared Barsky
(74) *Attorney, Agent, or Firm* — Fish & Richardson P.C.

(57) ABSTRACT

The present application provides, inter alia, a compound of Formula (I): or a pharmaceutically acceptable salt thereof, and methods of use of the compound of Formula (I) for treatment and prevention of cyanide poisoning.

7 Claims, 13 Drawing Sheets

(56) References Cited

OTHER PUBLICATIONS

Demchak et al., "Interleukin-2 and high-dose cisplatin in patients with metastatic melanoma: a pilot study," J. Clin. Oncol., Oct. 1991, 9(10):1821-1830.
Extended European Search Report in European Application No. 18783996.4, dated Nov. 16, 2020, 8 pages.
Fichtinger-Schepman et al., "Adducts of the antitumor drug cis-diamminedichloroplatinum(II) with DNA: formation, identification, and quantitation," Biochemistry, Jan. 1985, 24(3):707-713.
Fischer et al., "Cisplatin and dimethyl sulfoxide react to form an adducted compound with reduced cytotoxicity and neurotoxicity," Neurotoxicology, Mar. 2008, 29:444-452.
Frantz & Wipf, "Mitochondria as a target in treatment. Environ Mol Mutagen," Jun. 2010, 51(5):462-475.
Galan-Moya et al., "c-Abl activates p38 MAPK independently of its tyrosine kinase activity: Implications in cisplatin-based therapy," Int J Cancer, Jan. 2008 122(2):289-297.
Gopal et al., "d-Methionine protects against cisplatin-induced neurotoxicity in cortical networks," Neurotoxicol Teratol, Sep. 2012, 34(5):495-504.
Hall et al., "Say no to DMSO: dimethylsulfoxide inactivates cisplatin, carboplatin, and other platinum complexes," Cancer Res., Jul. 2014, 74(14):3913-3922.
Hall et al., "Sodium thiosulfate or hydroxocobalamin for the empiric treatment of cyanide poisoning?" Ann. Emerg. Med., Jun. 2007, 49(6):806-813.
Hall et al., "Which cyanide antidote?" Crit. Rev. Toxicol., 2009, 39(7):541-552.
Hao et al., "In vivo structure-activity relationship study of dorsomorphin analogues identifies selective VEGF and BMP inhibitors," ACS Chem. Biol. Feb. 2010, 5(2):245-253.
Harrap et al., "Antitumour, toxic and biochemical properties of cis-platin and eight other platinum complexes," Cisplatin: Current status and new developments, Prestayko et al. (eds.), Chapter 12, pp. 193-212.
Hayes et al., "High dose cis-platinum diammine dichloride: amelioration of renal toxicity by mannitol diuresis," Cancer, 1977, 39:1372-1381.
Helke et al., "Animal models of toxicology testing: the role of pigs," Expert Opin. Drug Metab. Toxicol., 2013, 9(2):127-139.
Ivanov et al., "Cisplatin binding sites on human albumin," J. Biol. Chem., Jun. 1998, 273(24):14721-14730.
Jamieson et al., "Structure, Recognition, and Processing of Cisplatin-DNA Adducts," Chem. Rev., 1999, 99:2467-2498.
Keilin, "Cytochrome and respiratory enzymes," Proceedings of the Royal Society B: Biological Sciences, Feb. 1929, 104(730):206-252.
Kimberly et al., "Metabolite profiling identifies anandamide as a biomarker of nonalcoholic steatohepatitis," JCI Insight, May 2017, 2(9):e92989.
Lee et al., "Noninvasive optical cytochrome c oxidase redox state measurements using diffuse optical spectroscopy," J. Biomed. Opt., May 2014, 19(5):055001.
Lee, et al., "Non-invasive in vivo diffuse optical spectroscopy monitoring of cyanide poisoning in a rabbit model," Physiol. Meas., 2007, 28:1057-1066.
MacRae et al., "A countermeasure development pipeline," Ann. N. Y. Acad. Sci., Aug. 2016, 1378(1):58-67.
Marraffa et al., "Antidotes for toxicological emergencies: a practical review," Am. J. Health-Syst. Pharm., Feb. 2012, 69:199-212.
Morocco, "Cyanides," Crit. Care Clin., Oct. 2005, 21(4):691-705.
Nath et al., "Chemical and metabolomic screens identify novel biomarkers and antidotes for cyanide exposure," FASEB J., May 2013, 27(5):1928-1938.
Nath et al., "Cisplatin Analogs Confer Protection against Cyanide Poisoning," Cell Chem. Biol., May 2017, 24:1-11.
Nogue-Xarau et al., "Acute chemical emergencies," N. Engl. J. Med., 2004, 350:2102-2104.
PCT International Preliminary Report on Patentability in International Application No. PCT/US2018/027361, dated Oct. 24, 2019, 8 pages.
Purser et al., "Intoxication by cyanide in fires: a study in monkeys using polyacrylonitrile," Arch. Environ. Health, 1984, 39(6):394-400.
Siddik, "Cisplatin: mode of cytotoxic action and molecular basis of resistance," Oncogene, Oct. 2003, 22:7265-7279.
Sousa et al., "Toxicokinetics of cyanide in rats, pigs and goats after oral dosing with potassium cyanide," Arch. Toxicol., 2003, 77:330-334.
Stathopoulos et al., "Liposomal cisplatin combined with paclitaxel versus cisplatin and paclitaxel in non-small-cell lung cancer: a randomized phase III multicenter trial," Ann. Oncol., Nov. 2010, 21(11):2227-2232.
Strumberg et al., "Evaluation of long-term toxicity in patients after cisplatin-based chemotherapy for non-seminomatous testicular cancer," Ann. Oncol., Feb. 2002, 13(2):229-236.
Thompson et al., "Cisplatin neuropathy. Clinical, electrophysiologic, morphologic, and toxicologic studies," Cancer, Oct. 1984, 54:1269-1275.
TOXNET, "Soduim chloroplatinate," ChemIDplus, retrieved from URL <https://chem.nlm.nih.gov/chemidplus/rn/1307-82-0>, 3 pages.
Wisnovsky et al., "Targeting mitochondrial DNA with a platinum-based anticancer agent," Chem. Biol., Nov. 2013, 20(11):1323-1328.
Yao et al., "Cisplatin nephrotoxicity: a review," Am. J. Med. Sci., Aug. 2007, 334(2):115-124.
Zhou et al., "A mitochondrion-targeting copper complex exhibits potent cytotoxicity against cisplatin-resistant tumor cells through multiple mechanisms of action," Chem. Sci., 2014, 5:2761-2770.
International Search Report and Written Opinion dated Jul. 30, 2018 in international application No. PCT/US2018/027361, 14 pgs.

* cited by examiner

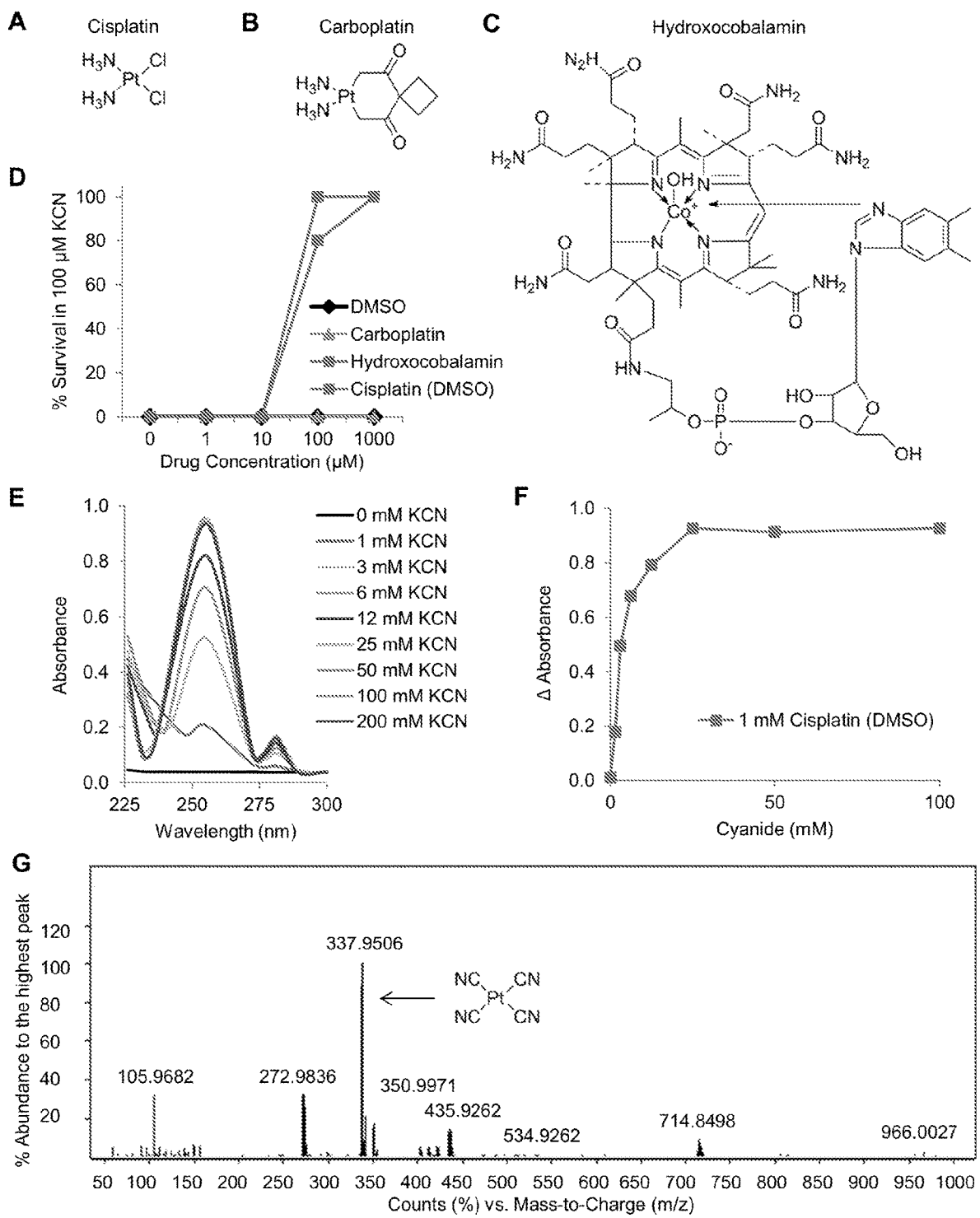
Figure 1. Platinum complexes act as antidotes to cyanide poisoning by binding the cyanide anion Figure 2. Structure activity relationships of cisplatin analogues

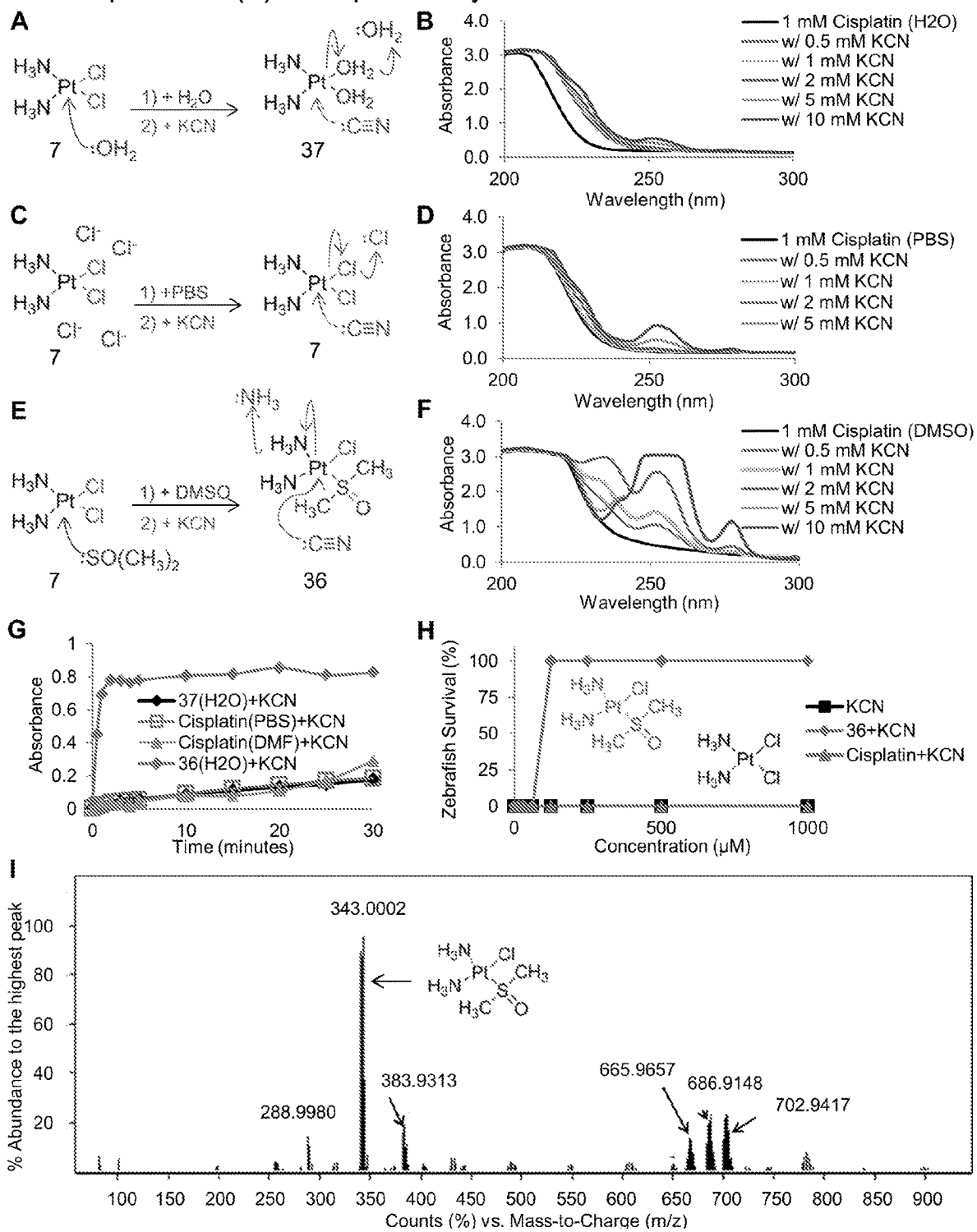
Figure 3. Identification of cis-diaminechloro(dimethylsulfoxide)platinum(II) as a potent cyanide antidote in zebrafish

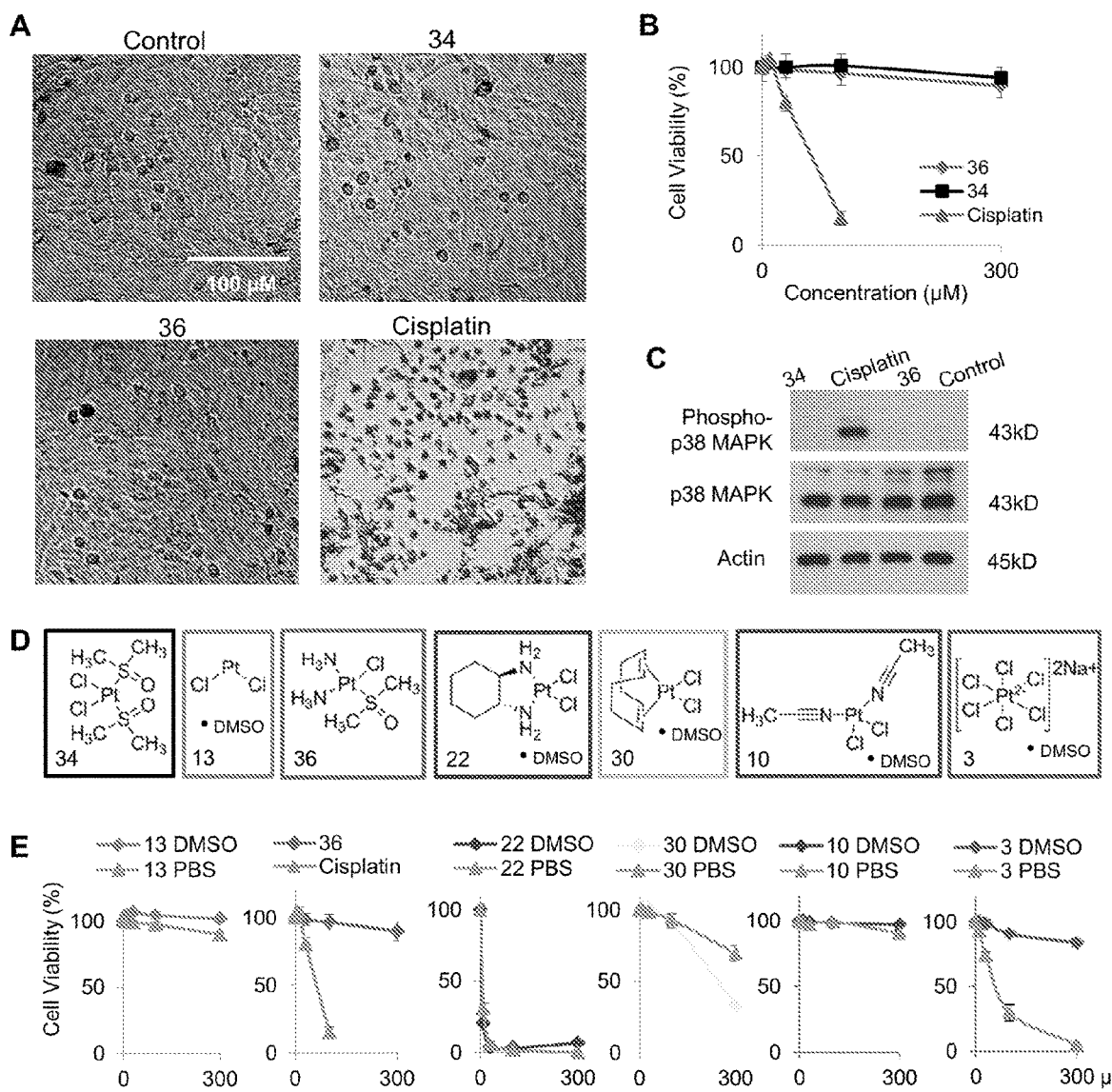
Figure 4. A subset of cisplatin analogues solvated in DMSO display decreased cytotoxicity in human cells Figure 5. Cisplatin analogues protected mice exposed to a lethal dose of cyanide
A
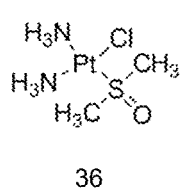
36
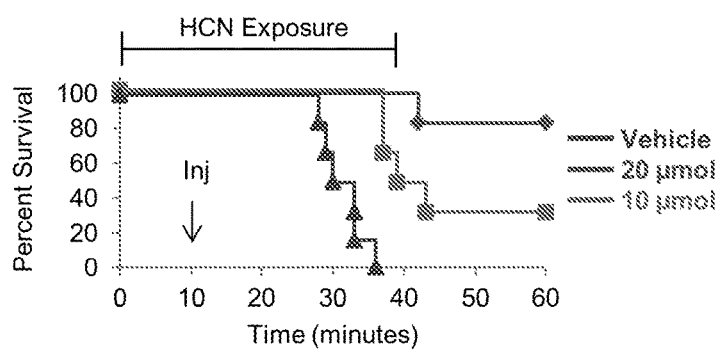
B
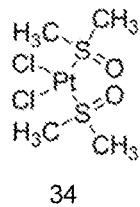
34
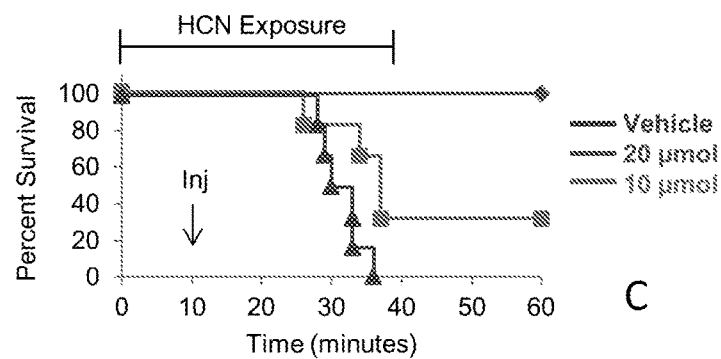
C
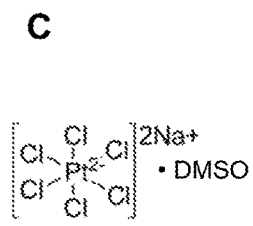
3
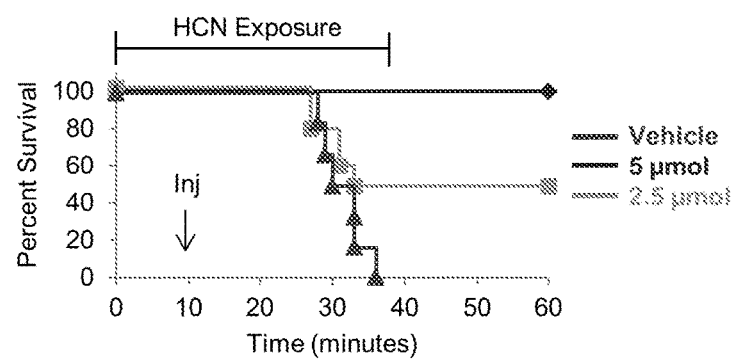

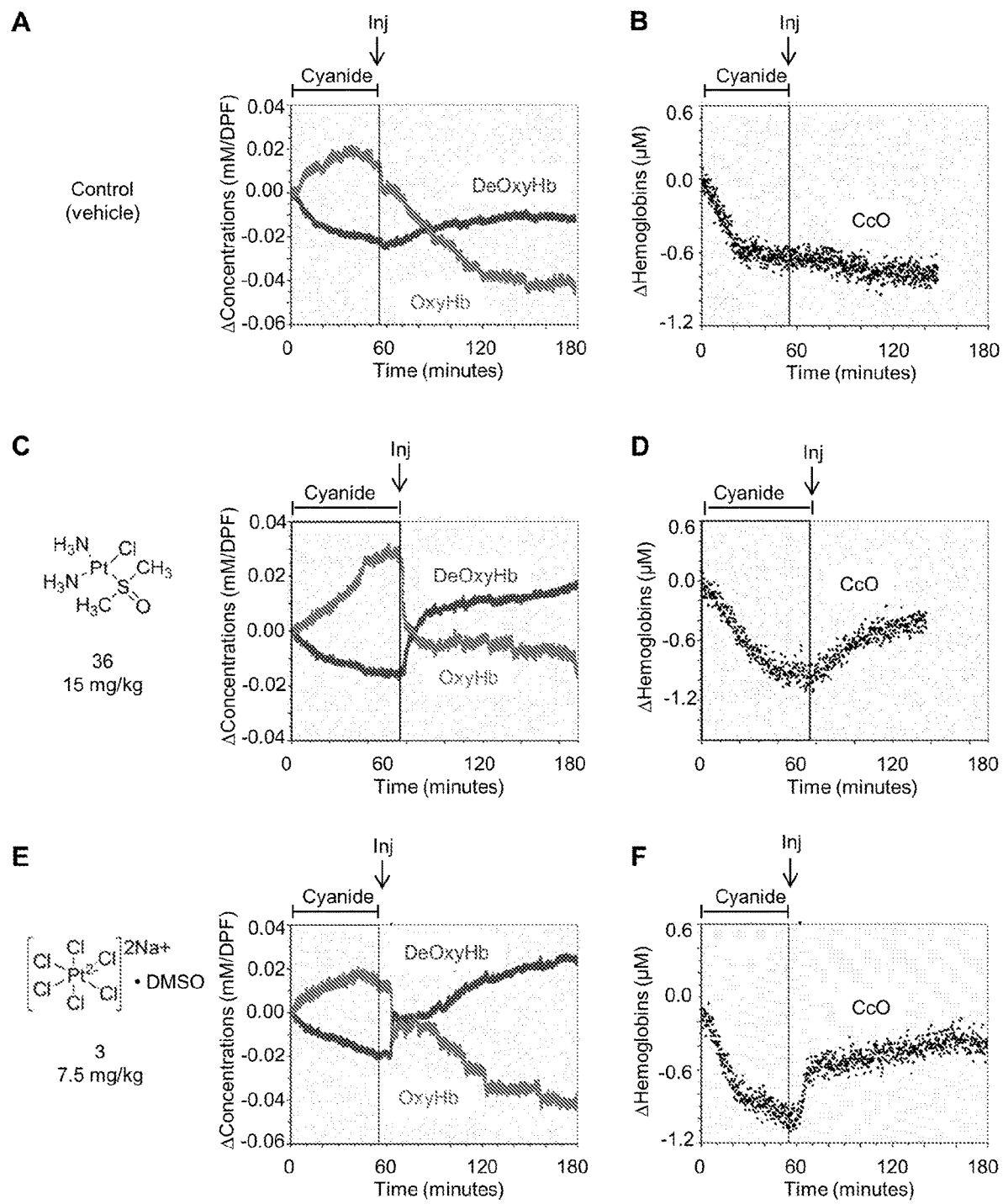
Figure 6. Cisplatin analogues reversed cyanide induced changes in oxidative metabolism in rabbits

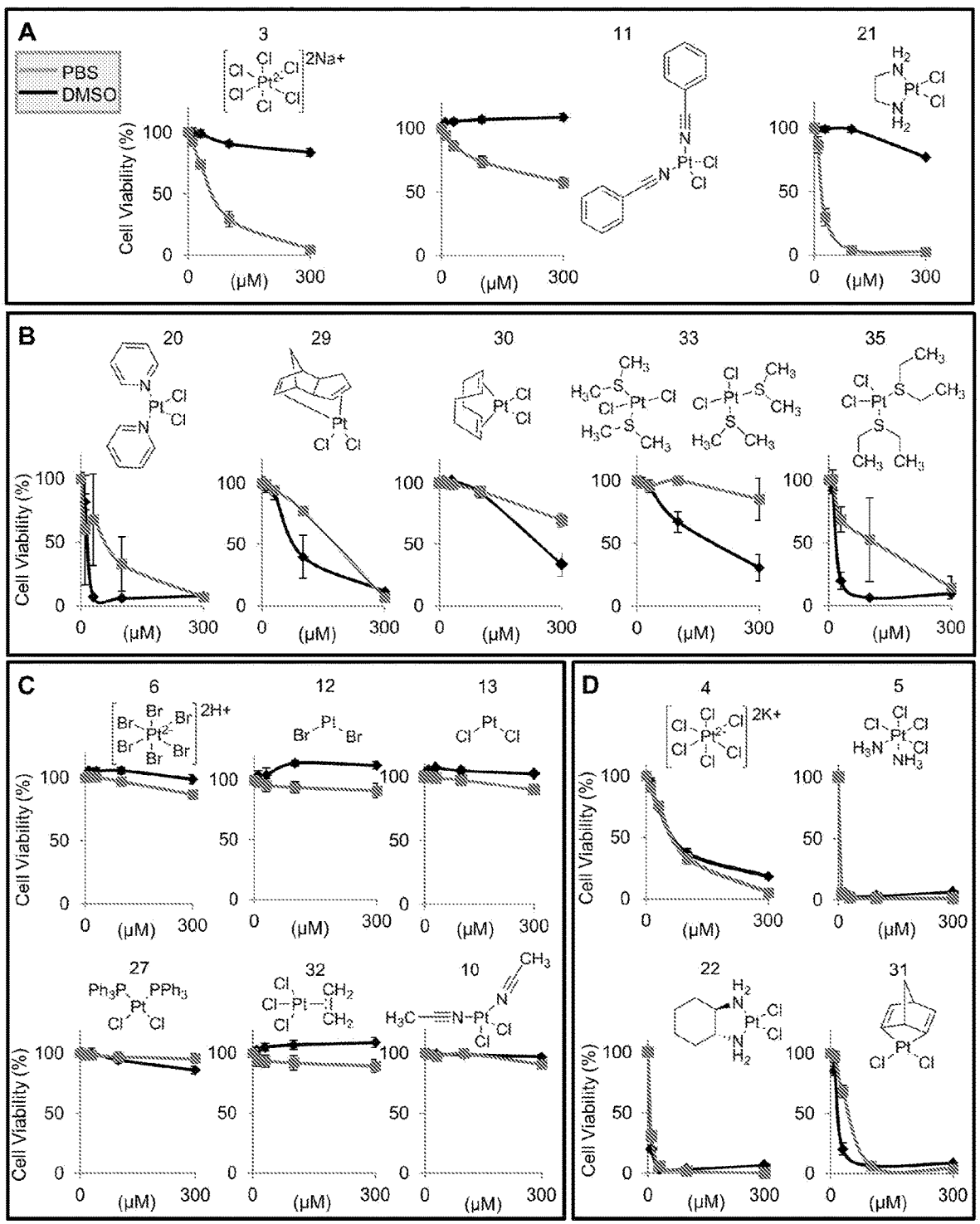
Figure 7. Cytotoxicity of cisplatin analogs in H1975 Cells.

Figure 8. Identification of the products generated by the reaction of hexachloroplatinate(IV) with DMSO and their capacity to bind cyanide anions.
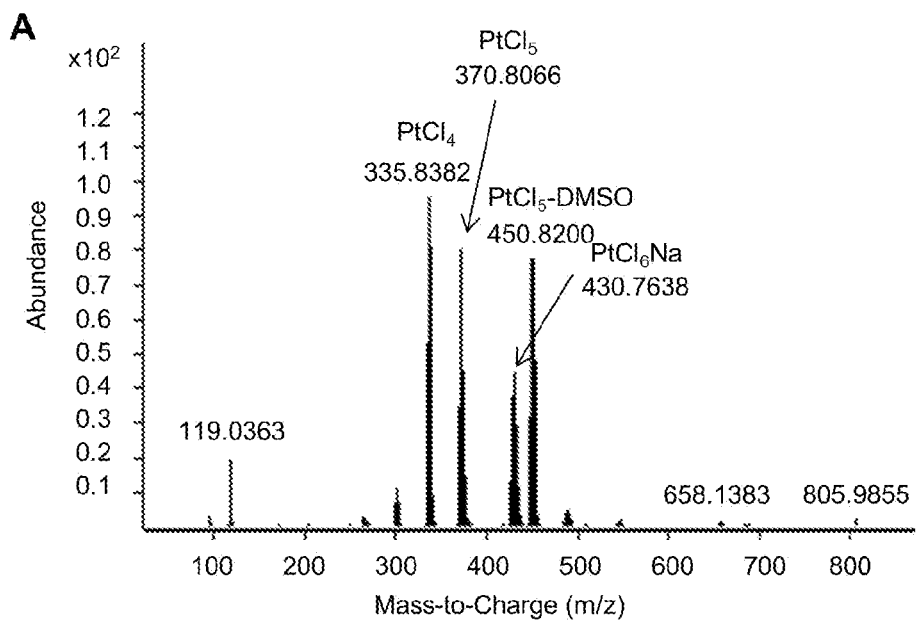
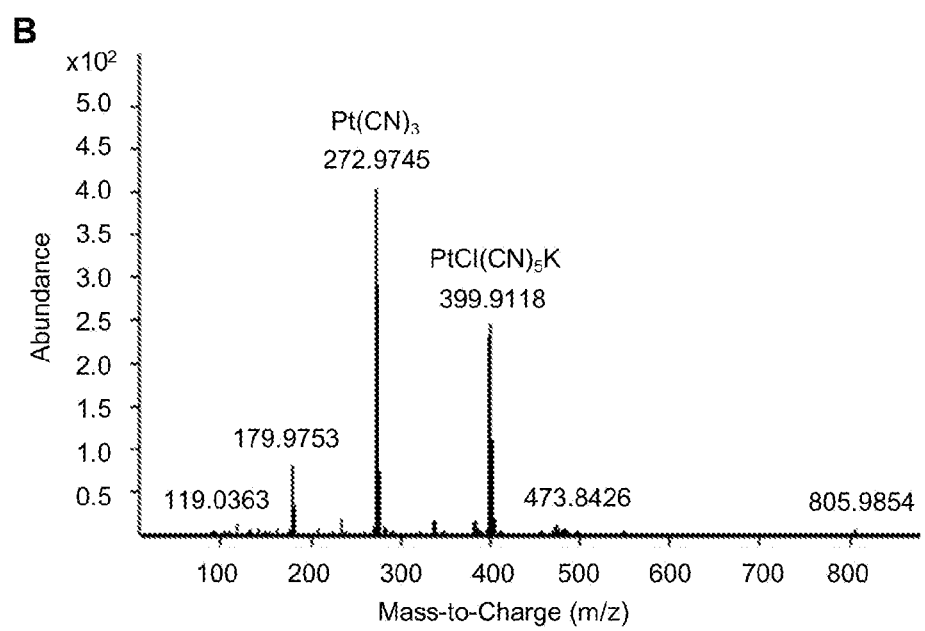

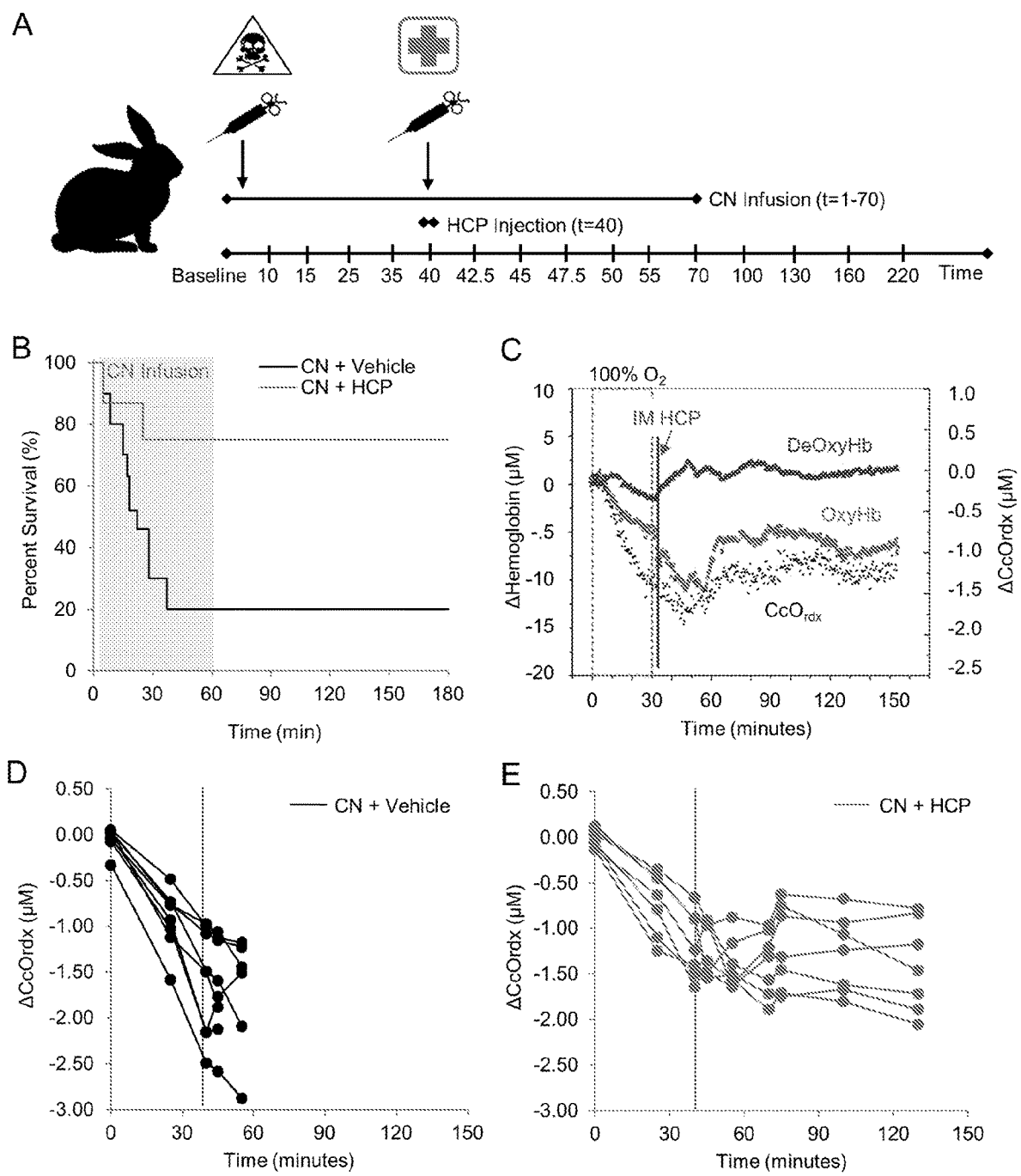
Figure 9. Intramuscular delivery of HCP-DMSO protects rabbits from a lethal dose of cyanide Figure 10. HCP alleviates cyanide induced blockage of the TCA cycle
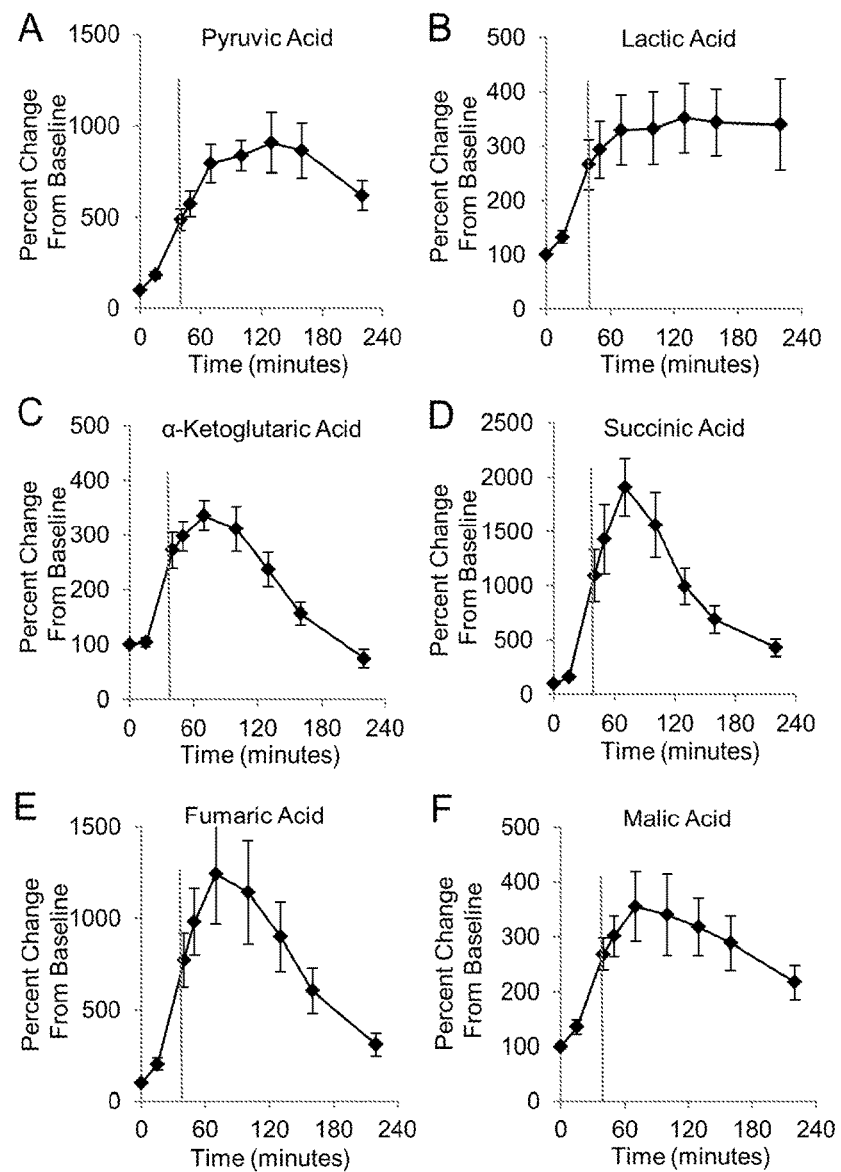

Intramuscular delivery of HCP is rapidly absorbed and scavenges multiple cyanide ions Figure 12. Surrogate biomarkers of adverse drug reactions do not change during acute HCP exposure in rabbits
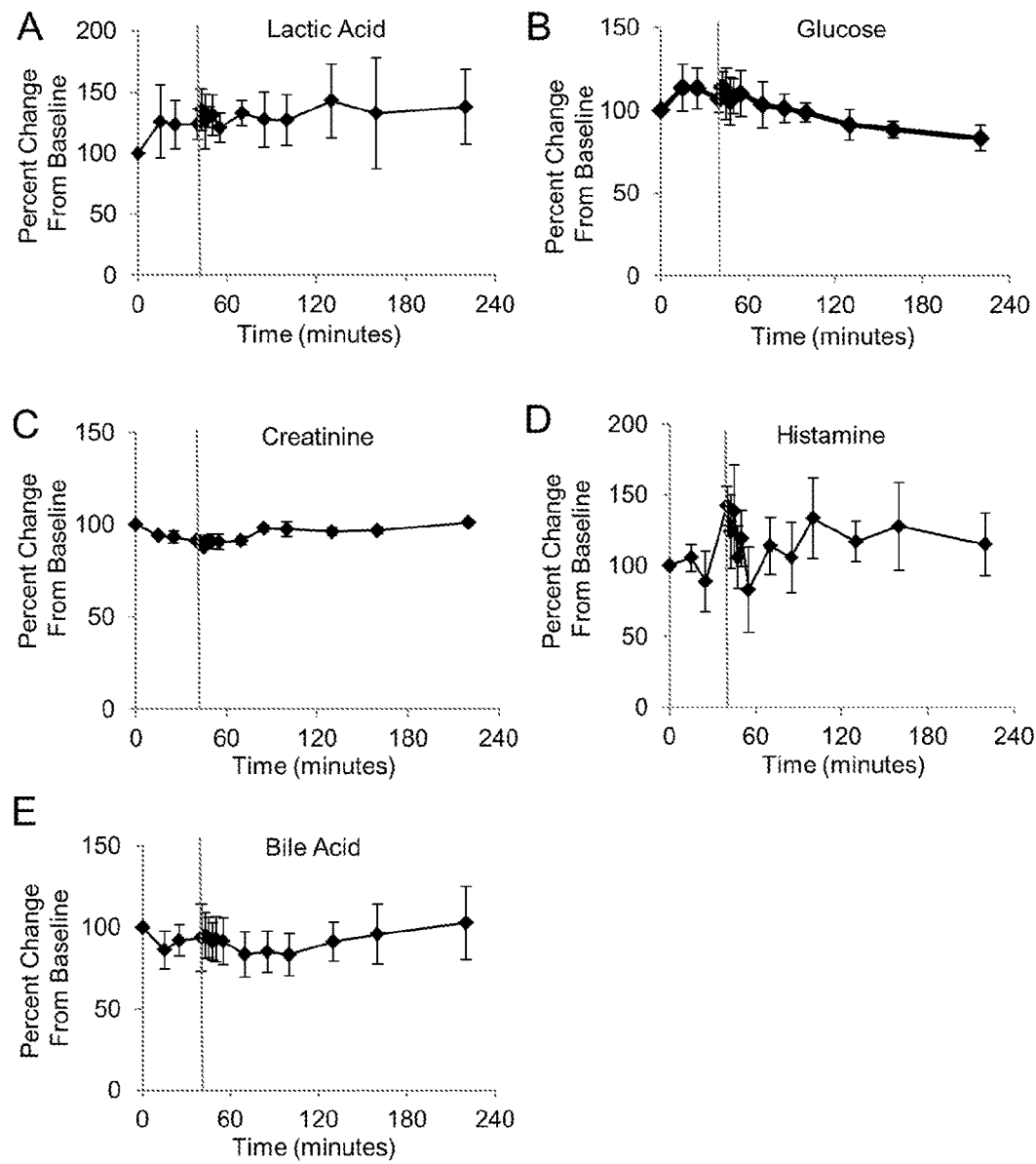

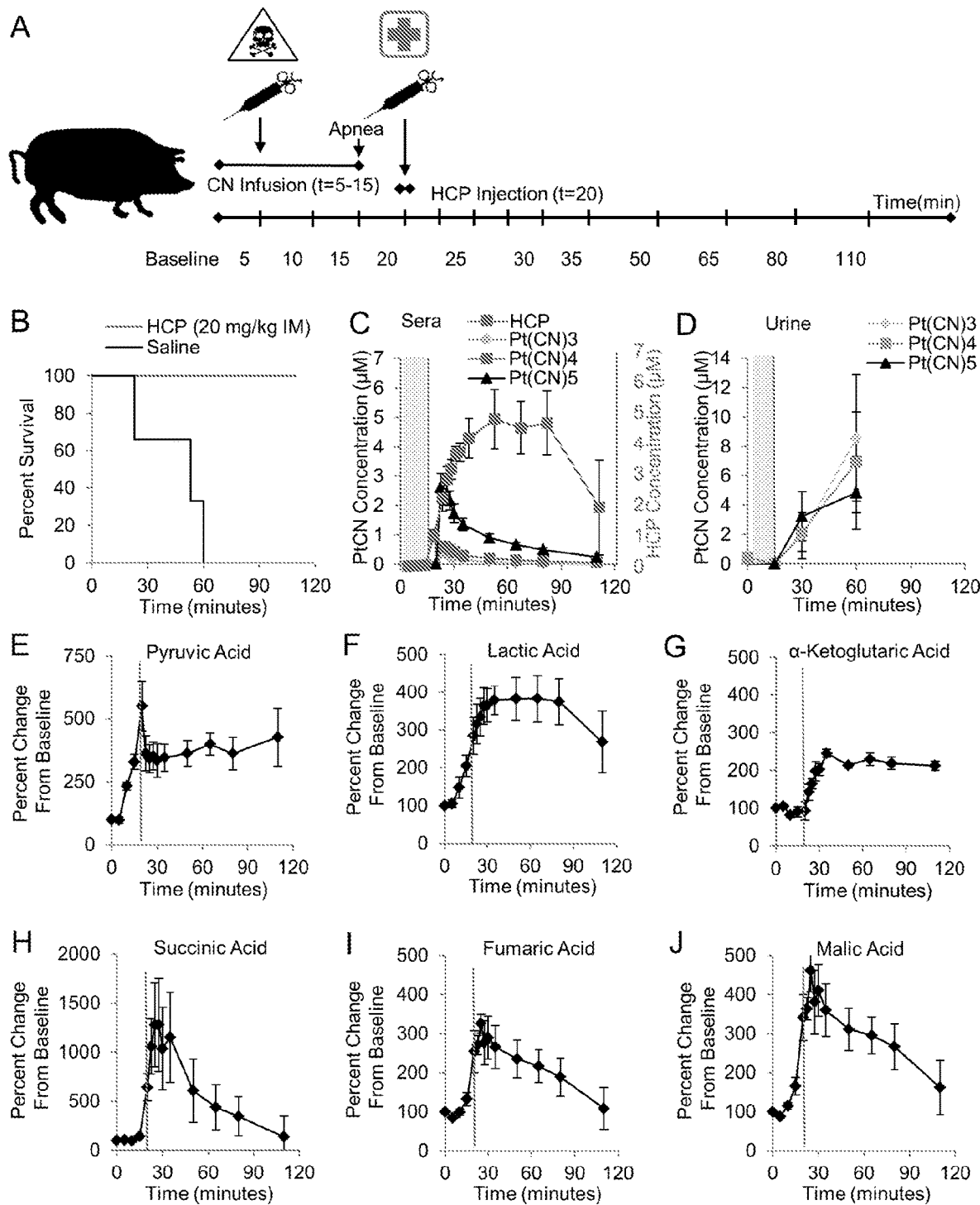
Figure 13. Replication of survival, pharmacokinetic and metabolite findings in a pilot study in a swine model of cyanide poisoning

ANTIDOTES TO CYANIDE POISONING

CLAIM OF PRIORITY

This application is a § 371 National Stage Application of PCT/US2018/027361, filed Apr. 12, 2018, which claims the benefit of U.S. Provisional Application No. 62/484,623, filed Apr. 12, 2017. The entire contents of the foregoing are hereby incorporated by reference.

STATEMENT REGARDING FEDERALLY SPONSORED RESEARCH OR DEVELOPMENT

This invention was made with government support under grant No. NIH/U54NS079201 awarded by National Institutes of Health (NIH). The government has certain rights in the invention.

TECHNICAL FIELD

This invention relates to antidotes to cyanide poisoning, and in particular to platinum compounds capable of binding cyanide anions.

BACKGROUND

Cyanide anion (CN⁻) is highly toxic due to its ability to disrupt electron transport chain in a cell leading to the cell's inability to aerobically produce ATP for energy. Cyanide kills organisms as diverse as insects, fish and humans within seconds to hours. The most common route of cyanide exposure in industrialized nations is smoke inhalation from fires leading to fatalities of about 23,000 per year in the United States. American industries utilize 300,000 tons of cyanide annually, heightening the risk of large-scale industrial accidents and chemical terrorism. The Department of Homeland Security has declared cyanide as a credible threat. Therefore, cyanide antidotes are of interest to first responders, clinicians, and the military and industrial manufactures that use cyanide to make their products.

SUMMARY

Cisplatin holds an illustrious position in the history of chemistry most notably for its role in the virtual cure of testicular cancer. The present application proves, inter alia, methods to use this small molecule in cyanide detoxification in vivo. The binding affinity of the cyanide anion for the positively charged metal platinum is creates an extremely stable complex in vitro. Hence, the present application provides diverse platinum-containing compounds that confer protection from cyanide poisoning in fish and mammals, and are effective antidotes for cyanide poisoning. Existing cyanide antidotes require intravenous administration and a hospital-like setting, while the cyanide antidotes described herein may be rapidly deployed, for example by intramuscular injection, and provide rapid, easily accessible, and highly effective management of cyanide poisoning.

In a first general aspect, the present disclosure provides a pharmaceutical composition comprising:
(i) a compound of Formula (I):

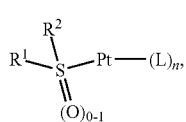

(I)

or a pharmaceutically acceptable salt thereof, wherein:
$R^1$ is selected from $C_{1-3}$ alkyl, $C_{1-3}$ haloalkyl, $C_{2-4}$ alkenyl, $C_{2-4}$ alkynyl, and $C_{6-10}$ aryl;
$R^2$ is selected from $C_{1-3}$ alkyl, $C_{1-3}$ haloalkyl, $C_{2-4}$ alkenyl, $C_{2-4}$ alkynyl, and $C_{6-10}$ aryl; or
$R^1$ and $R^2$ together form a group selected from $C_{1-3}$ alkylene, $C_{2-4}$ alkenylene, or $C_{2-4}$ alkynylene;
n is an integer selected from 1, 2, 3, 4, and 5;
each L is a ligand independently selected from halogen, $NR^{c1}R^{d1}$, $NR^{c1}R^{d1}R^{e1}$ $C_{2-12}$ alkene, $OR^{a1}$, $H_2O$, $HOR^3$, $NC-R^3$, $P(R^{a1})_3$, $S(O)_2R^1R^2$, $SR^1R^2$, and 5-10 membered heteroaryl; or
any two L together form a bidentate ligand selected from $C_{4-12}$ alkyldiene, 12-16 membered fused heteroaryl, and bis (5-10 membered heteroaryl);
each $R^{a1}$ is independently selected from H, $C_{1-6}$ alkyl, $C_{1-3}$ haloalkyl, $C_{2-4}$ alkenyl, $C_{2-4}$ alkynyl, and $C_{6-10}$ aryl;
each $R^{c1}$, $R^{d1}$, and $R^{e1}$ is independently selected from H, $C_{1-3}$ alkyl, $C_{1-3}$ haloalkyl, $C_{2-4}$ alkenyl, $C_{2-4}$ alkynyl, and $C_{3-10}$ cycloalkyl; or any two $R^{c1}$ together form a group selected from $C_{1-3}$ alkylene, $C_{2-4}$ alkenylene, and $C_{3-10}$ cycloalkylene; and
$R^3$ is selected from $C_{1-3}$ alkyl, $C_{1-3}$ haloalkyl, $C_{2-4}$ alkenyl, $C_{2-4}$ alkynyl, and $C_{6-10}$ aryl; and
ii) a pharmaceutically acceptable carrier.
Certain implementations of the first general aspects are described below.
In some embodiments, the compound of Formula (I) is selected from:

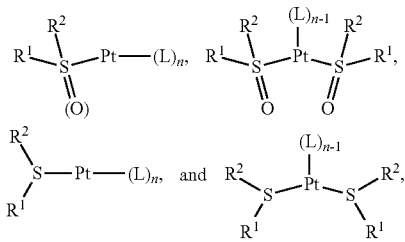

or a pharmaceutically acceptable salt thereof.
In some embodiments:
$R^1$ and $R^2$ are each independently $C_{1-3}$ alkyl,
n is an integer selected from 1, 3, and 5;
each L is independently selected from halogen, $NR^{c1}R^{d1}R^{e1}$, $C_{2-12}$ alkene, $NC-R^3$, $P(R^{a1})_3$, $S(O)_2R^1R^2$, $SR^1R^2$, and 5-10 membered heteroaryl; or
any two L together form a bidentate ligand selected from $C_{4-12}$ alkyldiene, 12-16 membered fused heteroaryl, and bis (5-10 membered heteroaryl);
each $R^{a1}$ is independently selected from $C_{1-6}$ alkyl and $C_{6-10}$ aryl;
each $R^{c1}$, $R^{d1}$, and $R^{e1}$ is independently selected from H, $C_{1-3}$ alkyl, and $C_{3-10}$ cycloalkyl; or
any two $R^{c1}$ together form a group selected from $C_{1-3}$ alkylene and $C_{3-10}$ cycloalkylene; and
$R^3$ is selected from $C_{1-3}$ alkyl and $C_{6-10}$ aryl.
In some embodiments:
$R^1$ and $R^2$ are each independently $C_{1-3}$ alkyl,
n is an integer selected from 1, 3, and 5;
each L is independently selected from halogen, $NR^{c1}R^{d1}R^{e1}$, $S(O)_2R^1R^2$, and $SR^1R^2$; and
each $R^{c1}$, $R^{d1}$, and $R^{e1}$ is independently selected from H and $C_{1-3}$ alkyl.

In some embodiments, the compound of Formula (I) is selected from:

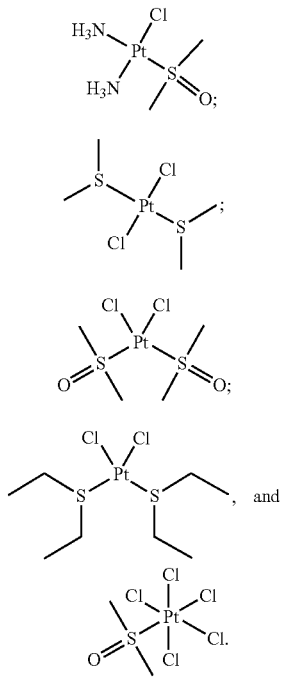

or a pharmaceutically acceptable salt thereof.

In some embodiments, the compound of Formula (I) is:

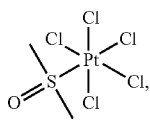

or a pharmaceutically acceptable salt thereof.

In some embodiments, the compound of Formula (I) is selected from:

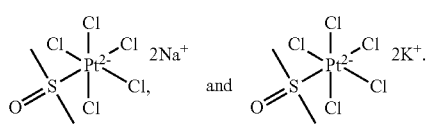

In some embodiments, the pharmaceutical composition is suitable for administration by an intramuscular injection.

In a second general aspect, the present disclosure provides the method comprising administering to a subject in need thereof a therapeutically effective amount of a pharmaceutical composition of the first general aspect.

Certain implementations of the second general aspect are described below.

In some embodiments, the method further comprises administering to the subject at least one additional therapeutic agent useful in treating or preventing cyanide poisoning.

In a third general aspect, the present disclosure provides a method of treating or preventing cyanide poisoning, the method comprising administering to a subject in need thereof a therapeutically effective amount of a compound of Formula (II):

or a pharmaceutically acceptable salt thereof, wherein:
each Hal is independently a halogen;
m is an integer selected from 0, 2, 3, and 4;
each L is a ligand independently selected from halogen, $NR^{c1}R^{d1}$, $NR^{c1}R^{d1}R^{e1}$, $C_{2-12}$ alkene, $OR^{a1}$, $H_2O$, $HOR^3$, $NC—R^3$, $P(R^{a1})_3$, $S(O)_2R^1R^2$, $SR^1R^2$, and 5-10 membered heteroaryl; or
any two L together form a bidentate ligand selected from $C_{4-12}$ alkyldiene, 12-16 membered fused heteroaryl, and bis(5-10 membered heteroaryl);
each $R^{a1}$ is independently selected from H, $C_{1-6}$ alkyl, $C_{1-3}$ haloalkyl, $C_{2-4}$ alkenyl, $C_{2-4}$ alkynyl, and $C_{6-10}$ aryl;
each $R^{c1}$, $R^{d1}$, and $R^{e1}$ is independently selected from H, $C_{1-3}$ alkyl, $C_{1-3}$ haloalkyl, $C_{2-4}$ alkenyl, $C_{2-4}$ alkynyl, and $C_{3-10}$ cycloalkyl; or
any two $R^{c1}$ together form a group selected from $C_{1-3}$ alkylene, $C_{2-4}$ alkenylene, and $C_{3-10}$ cycloalkylene; and
$R^3$ is selected from $C_{1-3}$ alkyl, $C_{1-3}$ haloalkyl, $C_{2-4}$ alkenyl, $C_{2-4}$ alkynyl, and $C_{6-10}$ aryl;
with the proviso that the compound of Formula (II) is not cisplatin.

Certain implementations of the third general aspect are described below.

In some embodiments, each Hal is independently selected from Cl and Br.

In some embodiments, the compound of Formula (II) is:

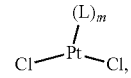

or a pharmaceutically acceptable salt thereof.

In some embodiments:
m is an integer selected from 0, 2, and 4;
each L is a ligand independently selected from halogen, $NR^{c1}R^{d1}R^{e1}$, $C_{2-12}$ alkene, $NC—R^3$, $P(R^{a1})_3$, $S(O)_2R^1R^2$, $SR^1R^2$, and 5-10 membered heteroaryl; or
any two L together form a bidentate ligand selected from $C_{4-12}$ alkyldiene, 12-16 membered fused heteroaryl, and bis(5-10 membered heteroaryl);
each $R^{a1}$ is independently selected from $C_{1-6}$ alkyl and $C_{6-10}$ aryl;
each $R^{c1}$, $R^{d1}$, and $R^{e1}$ is independently selected from H, $C_{1-3}$ alkyl, and $C_{3-10}$ cycloalkyl; or
any two $R^{c1}$ together form a group selected from $C_{1-3}$ alkylene and $C_{3-10}$ cycloalkylene; and
$R^3$ is selected from $C_{1-3}$ alkyl and $C_{6-10}$ aryl.

In some embodiments, at least one L is selected from $S(O)_2R^1R^2$ and $SR^1R^2$.

In some embodiments, the compound of Formula (II) is selected from:
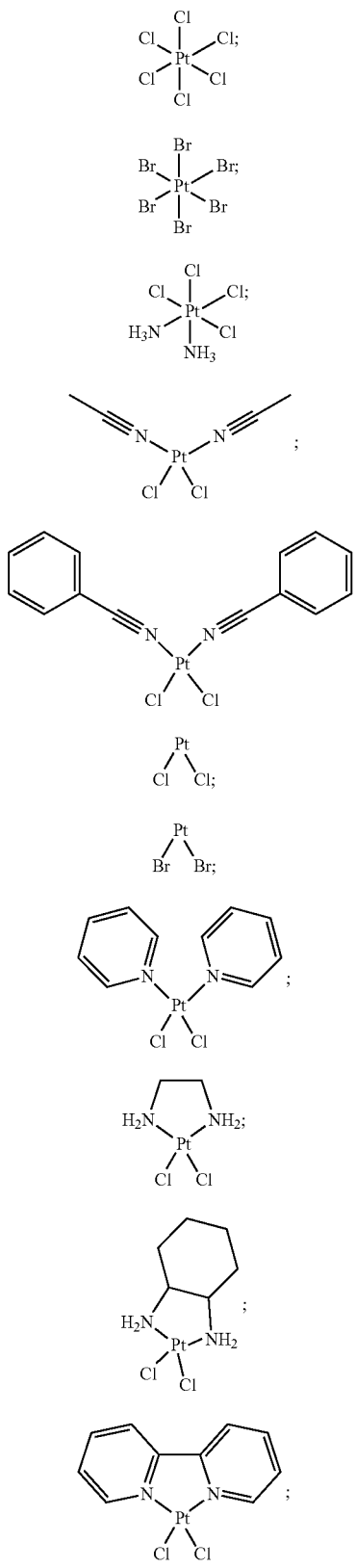
-continued
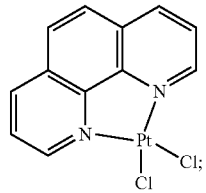
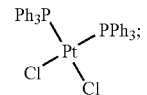
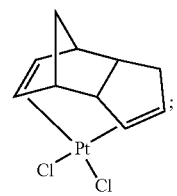
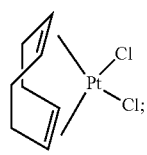
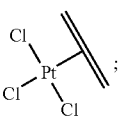
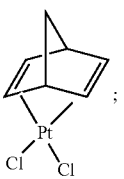
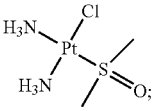
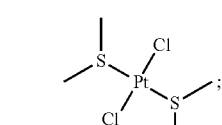
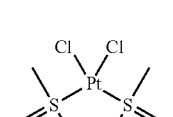
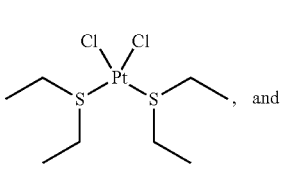

-continued

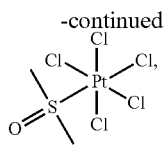

or a pharmaceutically acceptable salt thereof.

In some embodiments, the compound of Formula (II) is hexachloroplatinate of formula:

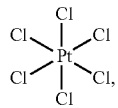

or a pharmaceutically acceptable salt thereof.

In some embodiments, the compound of Formula (II), or a pharmaceutically acceptable salt thereof, is administered to the subject by an intramuscular injection.

In some embodiments, the method further comprises administering to the subject at least one additional therapeutic agent useful in treating or preventing cyanide poisoning.

In a fourth general aspect, the present disclosure a cyanide antidote kit comprising:

(i) a container comprising a compound of Formula (II):

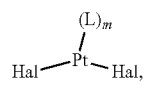

or a pharmaceutically acceptable salt thereof, wherein:
each Hal is independently a halogen;
m is an integer selected from 0, 2, 3, and 4;
each L is a ligand independently selected from halogen, $NR^{c1}R^{d1}$, $NR^{c1}R^{d1}R^{e1}$, $C_{2-12}$ alkene, $OR^{a1}$, $H_2O$, $HOR^3$, $NC-R^3$, $P(R^{a1})_3$, $S(O)_2R^1R^2$, $SR^1R^2$, and 5-10 membered heteroaryl; or any two L together form a bidentate ligand selected from $C_{4-12}$ alkyldiene, 12-16 membered fused heteroaryl, and bis (5-10 membered heteroaryl);

each $R^{a1}$ is independently selected from H, $C_{1-6}$ alkyl, $C_{1-3}$ haloalkyl, $C_{2-4}$ alkenyl, $C_{2-4}$ alkynyl, and $C_{6-10}$ aryl;

each $R^{c1}$, $R^{d1}$, and $R^{e1}$ is independently selected from H, $C_{1-3}$ alkyl, $C_{1-3}$ haloalkyl, $C_{2-4}$ alkenyl, $C_{2-4}$ alkynyl, and $C_{3-10}$ cycloalkyl; or any two $R^{c1}$ together form a group selected from $C_{1-3}$ alkylene, $C_{2-4}$ alkenylene, and $C_{3-10}$ cycloalkylene; and $R^3$ is selected from $C_{1-3}$ alkyl, $C_{1-3}$ haloalkyl, $C_{2-4}$ alkenyl, $C_{2-4}$ alkynyl, and $C_{6-10}$ aryl; and (ii) a container comprising dimethyl sulfoxide (DMSO).

Certain implementations of the fourth general aspect are described below.

In some embodiments, each Hal is independently selected from Cl and Br.

In some embodiments, the compound of Formula (II) is:

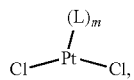

or a pharmaceutically acceptable salt thereof.

In some embodiments:

m is an integer selected from 0, 2, and 4;

each L is a ligand independently selected from halogen, $NR^{c1}R^{d1}R^{e1}$, $C_{2-12}$ alkene, $NC-R^3$, $P(R^{a1})_3$, and 5-10 membered heteroaryl; or any two L together form a bidentate ligand selected from $C_{4-12}$ alkyldiene, 12-16 membered fused heteroaryl, and bis (5-10 membered heteroaryl);

each $R^{a1}$ is independently selected from $C_{1-6}$ alkyl and $C_{6-10}$ aryl;

each $R^{c1}$, $R^{d1}$, and $R^{e1}$ is independently selected from H, $C_{1-3}$ alkyl, and $C_{3-10}$ cycloalkyl; or any two $R^{c1}$ together form a group selected from $C_{1-3}$ alkylene and $C_{3-10}$ cycloalkylene; and $R^3$ is selected from $C_{1-3}$ alkyl and $C_{6-10}$ aryl.

In some embodiments, the compound of Formula (II) is selected from:

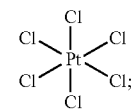
(3)

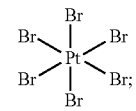
(6)

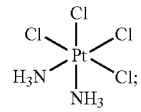
(5)

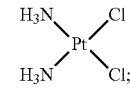
(7)

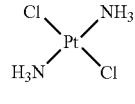
(8)

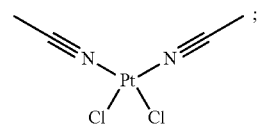
(10)

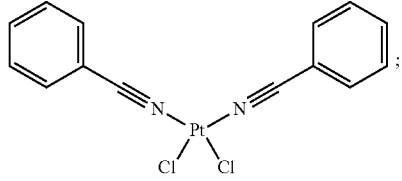
(11)

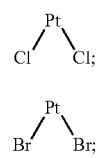
(13)

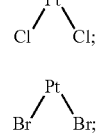
(12)

(20) 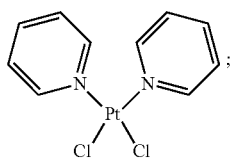

(21) 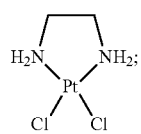

(22) 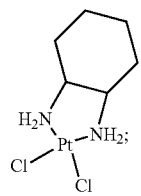

(23) 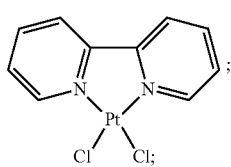

(24) 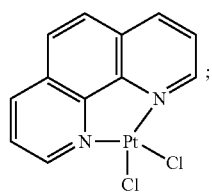

(27) 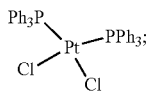

(29) 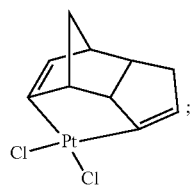

(30) 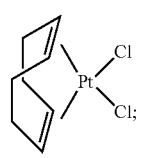

(32) 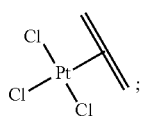

(31) 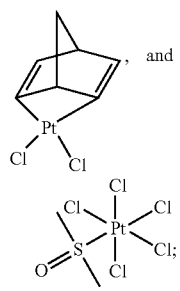

or a pharmaceutically acceptable salt thereof.

In some embodiments, the compound of Formula (II) is cisplatin:

(7) 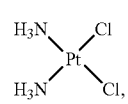

or a pharmaceutically acceptable salt thereof.

In some embodiments, the compound of Formula (II) is hexachloroplatinate:

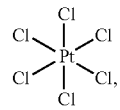

or a pharmaceutically acceptable salt thereof.

In some embodiments, the kit comprises a container comprising a pharmaceutically acceptable carrier.

In some embodiments, the kit further comprises written instructions to mix the compound of Formula (II), or a pharmaceutically acceptable salt thereof, and the dimethyl sulfoxide (DMSO).

In some embodiments, the kit further comprises a container comprising an additional therapeutic agent useful in treatment or prevention of cyanide poisoning.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the present application will be apparent from the following detailed description and figures, and from the claims.

DESCRIPTION OF DRAWINGS

FIGS. 1A-1G. Platinum complexes act as antidotes to cyanide poisoning by binding the cyanide anion. Chemical structure of 1A) cisplatin, 1B) carboplatin, and 1C) hydroxocobalamin. Compounds were dissolved in DMSO for the assays in this FIG. 1D) The effects of compounds on the survival of zebrafish exposed to 100 µM KCN. 1E) UV-VIS spectral shift data demonstrating the binding of the cisplatin to cyanide. 1F) Plot of the change in absorbance of 1 mM cisplatin over increasing concentrations of cyanide. 1G) Analysis by mass spectrometry demonstrates that cisplatin binds 4 cyanide anions. Also see Table 1.

FIG. 2. Antidote potency of platinum compounds. A panel of 35 platinum compounds was grouped into the following classes: platinum (IV) (1-6), square planar (7-13), FDA approved (14-19), pyridine (20-24), triphenylphosphine (25-28), alkene (29-32), and sulfur-containing complexes (33-35). A ten point dose curve ranging from 1-1000 µM was tested. The doses that rescued 100% of zebrafish ($EC_{100}$) from a challenge with 100 µM KCN were determined. The $EC_{100}$ was determined in both DMSO and PBS solvents (top and middle values, respectively). In a separate assay, the doses that caused 100% lethality ($LD_{100}$) in the absence of KCN were determined for complexes dissolved in DMSO (bottom value). NA indicates instances in which the complex did not induce any toxicity or did not rescue cyanide lethality at any of the doses tested.

FIGS. 3A-3I. Identification of cis-diamminechloro(dimethylsulfoxide) platinum(II) as a potent cyanide antidote in zebrafish. 3A) Depiction of the associative substitution reaction of water with cisplatin (7), and cyanide with the aquated form of cisplatin (Ref. 37). 3B) Spectral shift data demonstrating minimal binding of the aquated form of cisplatin to increasing concentrations of cyanide. 3C) Depiction of the solvation effect of PBS on cisplatin, and the associative substitution reaction of cyanide with cisplatin (7). 3D) Spectral shift data demonstrating minimal binding of cisplatin to increasing concentrations of cyanide. 3E) Depiction of the associative substitution reaction of DMSO with cisplatin generating complex 36, and cyanide with complex 36. 3F) Spectral shift data demonstrating binding of complex 36 to increasing concentrations of cyanide. 3G) Graph of the binding of 1 mM complex 37, complex 7, complex 36, and cisplatin dissolved in DMF to 5 mM cyanide over time, demonstrating the rapid and increased binding rate of complex 36 to cyanide. 3H) Survival assay in zebrafish demonstrating that complex 36 is a cyanide antidote while cisplatin is not an antidote. 3I) Mass spectrometry identification of cis-diamminechloro(dimethylsulfoxide)platinum(II) (complex 36) as the species created by the associative substitution reaction between DMSO and cisplatin. See also Table 2.

FIGS. 4A-4E. A subset of platinum compounds solvated in DMSO exhibit decreased cytotoxicity in human cells. 4A) Images of H1975 cells treated with vehicle, 34, 36, or cisplatin. 4B) Cell viability over increasing concentrations of 36, cisplatin and 34. Data represented as the mean±SD. 4C) Western blots for phospho-p38 MAPK on lysates from cells treated with vehicle, 34, 36, or cisplatin. Complexes from each structural class (4D) were dissolved in PBS or DMSO and cell viability over increasing concentrations was determined (4E). Also see FIG. 7.

FIGS. 5A-C. Platinum compounds protected mice exposed to a lethal dose of cyanide. Mice were exposed to cyanide gas for 15 min, injected with the indicated complex (Inj) and placed back in the gas chamber for another 25 min. The data are shown as percent survival versus time. The animals injected with vehicle consistently died between 30-35 minutes however 5A) 83% of mice treated with 20 µmol of 36, 5B) 100% of mice treated with 20 µmol of 34, and 5C) 100% of mice treated with 5 µmol of 3 survived exposure to a lethal dose of cyanide. n=6. Also see FIG. 8.

FIGS. 6A-6F. Platinum compounds reversed cyanide induced changes in oxidative metabolism in rabbits. A representative rabbit injected with cyanide demonstrating 6A) increased concentration of hemoglobin in the oxygenated state compared to the deoxygenated state in the CNS and B) decreased cytochrome oxidase c redox ratio in the muscle. Injection of 36 (6C-6D) or 3 (6E-6F) after the cyanide infusion results in rapid reversal of cyanide induced pathophysiologic changes. n=5.

FIGS. 7A-7D. Cytotoxicity of cisplatin analogs in H1975 Cells. Antidotes identified in the SAR study were solvated in DMSO or PBS and assessed for cytotoxicity in H1975 cells. 7A) DMSO inactivated the cytotoxic activity of complex 3, 11 and 21 while maintaining or improving their efficacy as cyanide antidotes. 7B) Complexes 20, 29, 30, 33 and 35 displayed increased ability to induce cell death when solvated in DMSO compared to PBS. 7C) Complexes 6, 10, 12, 13, 27 and 32 displayed minimal ability to induce cell death in both DMSO and PBS formulations at doses up to 300 µM. 7D) Complexes 4, 5, 22 and 31, in both PBS and DMSO formulations were more cytotoxic than cisplatin. Data represented as the mean±SEM.

FIGS. 8A-8B. Identification of the products generated by the reaction of hexachloroplatinate(IV) with DMSO and their capacity to bind cyanide anions. 8A) To decipher the chemical species created when hexachloroplatinate(IV) is dissolved in DMSO, we used ESI-MS. DMSO undergoes nucleophilic attack of the platinum atom, displacing one chloride ligand and generating PtCl5-DMSO (m/z=450). An ion signal detected at m/z=430 corresponds to the starting material (PtCl6Na). 8B) When cyanide is add to hexachloroplatinate(IV) that has been dissolved in DMSO the most abundant ion signals detected were at m/z=272 and 399 corresponding to the platinum atom bound to 3 or 5 cyanide anions.

FIGS. 9A-9E. Intramuscular delivery of HCP-DMSO protects rabbits from a lethal dose of cyanide. 9A) Overview of experimental procedure in the rabbit cyanide model. 9B) Kaplan-Meier plot of HCP (n=9; red) and vehicle (n=11; black) treated rabbits exposed to a lethal dose of cyanide. 9C) Oxygenation hemoglobin, deoxygenated hemoglobin, and cytochrome c oxidase redox state in the muscle of a representative rabbit treated with HCP. ΔCytochrome c oxidase redox (µM) in rabbits treated with cyanide and administered 9D) saline or 9E) HCP (line denotes when saline or HCP was delivered).

FIGS. 10A-10F. HCP-DMSO alleviates cyanide-induced blockage of the TCA cycle. Levels of 10A) pyruvic acid, 10B) lactic acid, 10C) α-ketoglutaric acid, 10D) succinic acid, 10E) fumaric acid, and 10F) malic acid in rabbits treated with cyanide (at t=1) and given HCP (at t=40 minute, n=9). Red line denotes when antidote was delivered. Data was normalized to baseline and presented as mean±SEM.

FIGS. 12A-12E. Surrogate biomarkers of adverse drug reactions do not change during acute HCP-DMSO exposure in rabbits. Levels of 12A) lactic acid, 12B) glucose, 12C) creatinine, 12D) histamine, and 12E) bile acids in rabbits treated with HCP for 220 minutes. Red line denotes when HCP was delivered. Data was normalized to baseline and presented as mean±SEM.

FIGS. 13A-13J. Replication of survival, pharmacokinetic and metabolite findings in a pilot study in a swine model of cyanide poisoning. A) Overview of experimental procedure in the swine cyanide model. B) Kaplan-Meier plot of HCP and vehicle treated pigs exposed to a lethal dose of cyanide. Pharmacokinetic profile of HCP and HCP-cyanide species in the sera (C) and urine (D) of pigs (n=3). Levels of E) pyruvic acid, F) lactic acid, G) α-ketoglutaric acid, H) succinic acid, I) fumaric acid, and J) malic acid in pigs treated with cyanide (at t=1) and given HCP (at t=20 minute, n=3).

DETAILED DESCRIPTION

Figure 11:
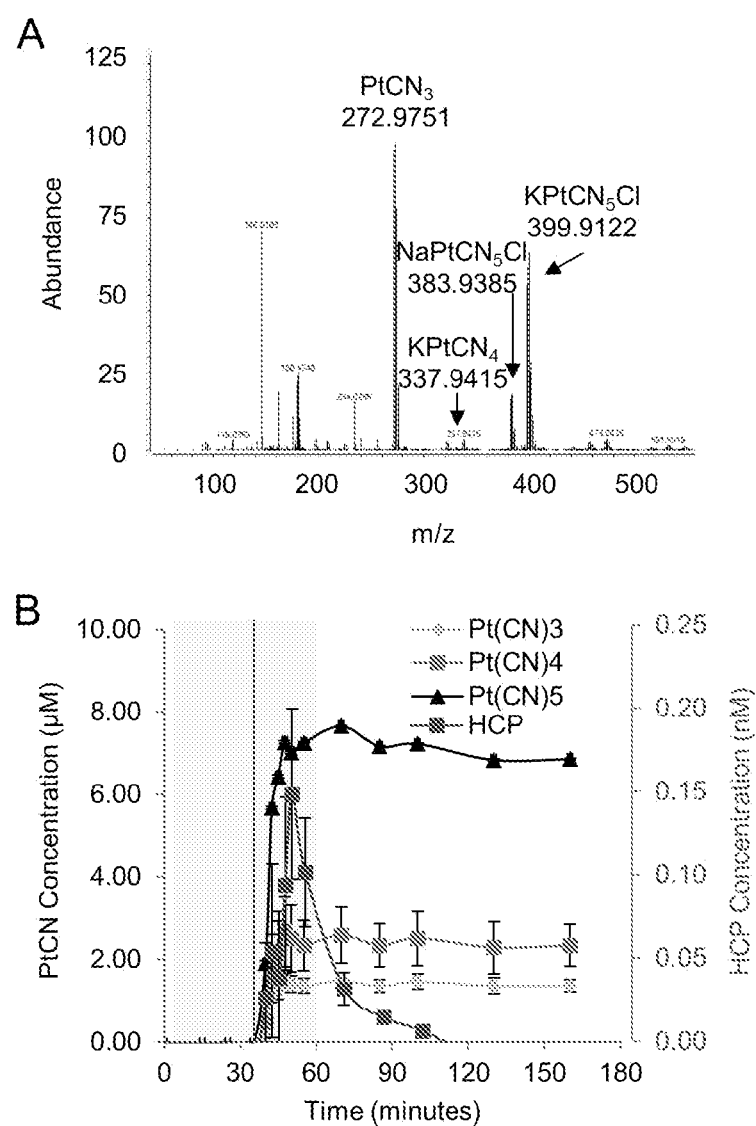
FIGS. 11A-11B. Intramuscular delivery of HCP-DMSO is rapidly absorbed and scavenges multiple cyanide ions. 11A) Representative mass spectrograph of antidote-cyanide profile in rabbit sera. 11B) Pharmacokinetic profile of HCP and HCP-cyanide species in the sera of rabbits (n=9).

Historically, cyanide has been an agent of murder, war and terrorism; however unintentional exposures are equally possible and lethal. Smoke inhalation is the most common cause of cyanide poisoning in western countries (Ref. 4). Cyanide reversibly binds to cytochrome c oxidase within the mitochondria (Ref 22). Consequently, electron transport and oxidative phosphorylation are halted, with resultant shifts of cellular metabolism from aerobic to anaerobic. If not reversed, the cessation of aerobic metabolism causes a fatal deficit in oxygen consumption. As such, cyanide is most toxic to organs with high metabolic requirements, such as the brain and heart. Milligram quantities of cyanide causes convulsions, seizures, cardiovascular collapse, and death in minutes, while lower doses can cause a spectrum of debilitating, longlasting pathologies, including a Parkinson-like syndrome due to irreversible neuronal death in select brain areas. Manufacturers in the United States produce 300,000 tons of hydrogen cyanide annually which is used in the extraction of gold during mining and in the synthesis of dyes, synthetic fibers, and plastics, as well as in warehouses as a pesticide. The thermal breakdown of materials such as wool, plastic, and synthetic polymers produce cyanide gas in addition to isocyanates (potent respiratory irritants), leading to smoke inhalation fatalities of approximately 5,000-10,000 and injuries of 23,000 per year in the United States (Ref. 1).

Industrial accidents are another major source of cyanide morbidity and mortality. The Bhopal disaster, considered the world's worst industrial accident, occurred when 45 tons of methyl isocyanate and hydrogen cyanide escaped from reservoirs killing nearly 4,000 people immediately, followed by another 15,000-20,000 individuals over the next few weeks, and leaving a half a million survivors with debilitating injuries such as chronic respiratory illnesses and blindness (Ref 8). Cyanide exposure can also occur as a consequence of consumption of cyanide-containing food and certain therapeutic drugs (e.g., nitroprusside).

Though there are two available antidotes for cyanide poisoning, their formulation and mode of action require them to be administered intravenously in hospital settings, therefore they would not be amenable to a mass causality scenario such as the Bhopal disaster (Ref 16). Current therapies for cyanide exposure include combinations of cobinamide, methemoglobin, thiosulfate, 3-mercaptopyruvate, inhaled amyl nitrite, infused sodium nitrite, and infused sodium thiosulfate, and infused hydroxocobalamin. These therapies can be effective for individual victims who have not succumbed to exposure, as the mechanisms of action involve binding, sequestration, and removal of cyanide from the blood. However, the utility of these therapies in mass exposure events or during field operations is limited by the complexities of intravenous administration and the requirement for ongoing monitoring from trained medical personnel due to the risk of dangerous decreases in blood pressure and anaphylaxis. Hydroxocobalamin stoichiometry only allows for equimolar amounts of cyanide to be bound by the drug. The treatment is limited by its low solubility in water, therefore necessitating large volumes of drug administration to counteract cyanide toxicity. In contrast, the Pt complexes of the present application bind up to 5 cyanide anions, improving the stoichiometry for binding multiple cyanide anions when compared to existing chelators or other antidotes.

The present application provides cyanide antidotes that are soluble, non-toxic, efficacious, and amendable for mass distribution and administration to affected individuals, to prevent the morbidity and mortality from smoke inhalation, industrial accidents, exposure to cyanide in the context of clinical sodium nitroprusside infusion, and the threat to soldiers fighting nonconventional conflicts.

Therapeutic Compounds

In some embodiments, the compounds of the present application are coordination complexes containing three components: (1) a positively charged metallic atom that is the coordination center; (2) ligands that are leaving groups (e.g., groups that may be replaced by cyanide); and (3) ligands that remain conjugated to the platinum atom (e.g., groups that remain conjugated to the metal in the presence of cyanide).

In some embodiments, the present application provides a compound of Formula (I):

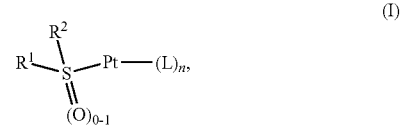

or a pharmaceutically acceptable salt thereof, wherein:

$R^1$ is selected from $C_{1-3}$ alkyl, $C_{1-3}$ haloalkyl, $C_{2-4}$ alkenyl, $C_{2-4}$ alkynyl, and $C_{6-10}$ aryl;

$R^2$ is selected from $C_{1-3}$ alkyl, $C_{1-3}$ haloalkyl, $C_{2-4}$ alkenyl, $C_{2-4}$ alkynyl, and $C_{6-10}$ aryl; or $R^1$ and $R^2$ together form a group selected from $C_{1-3}$ alkylene, $C_{2-4}$ alkenylene, or $C_{2-4}$ alkynylene;

n is an integer selected from 1, 2, 3, 4, and 5;

each L is a ligand, and at least one L is a leaving group.

In some embodiments, each L is a ligand independently selected from halogen, $NR^{c1}R^{d1}$, $NR^{c1}R^{d1}R^{e1}$, $C_{2-12}$ alkene, $OR^{a1}$, $H_2O$, $HOR^3$, $NC-R^3$, $P(R^{a1})_3$, $S(O)_2R^1R^2$, $SR^1R^2$, and 5-10 membered heteroaryl; or any two L together form a bidentate ligand selected from $C_{4-12}$ alkyldiene, 12-16 membered fused heteroaryl, and bis (5-10 membered heteroaryl);

each $R^{a1}$ is independently selected from H, $C_{1-6}$ alkyl, $C_{1-3}$ haloalkyl, $C_{2-4}$ alkenyl, $C_{2-4}$ alkynyl, and $C_{6-10}$ aryl;

each $R^{c1}$, $R^{d1}$, and $R^{e1}$ is independently selected from H, $C_{1-3}$ alkyl, $C_{1-3}$ haloalkyl, $C_{2-4}$ alkenyl, $C_{2-4}$ alkynyl, and $C_{3-10}$ cycloalkyl; or any two $R^{c1}$ together form a group selected from $C_{1-3}$ alkylene, $C_{2-4}$ alkenylene, and $C_{3-10}$ cycloalkylene; and $R^3$ is selected from $C_{1-3}$ alkyl, $C_{1-3}$ haloalkyl, $C_{2-4}$ alkenyl, $C_{2-4}$ alkynyl, and $C_{6-10}$ aryl.

In some embodiments, the compound of Formula (I) is:

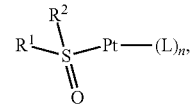

or a pharmaceutically acceptable salt thereof.

In some embodiments, the compound of Formula (I) is:

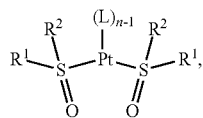

or a pharmaceutically acceptable salt thereof.

In some embodiments, the compound of Formula (I) is:

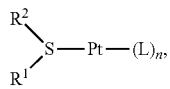

or a pharmaceutically acceptable salt thereof.

In some embodiments, the compound of Formula (I) is:

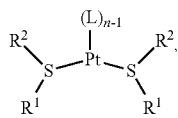

or a pharmaceutically acceptable salt thereof.

In some embodiments, the core Pt atom is Pt(II). In other embodiments, the core Pt atom is Pt(IV). In some embodiments, the oxidation state of the core Pt atom is selected from +1, +2, +3, +4, and −2.

In some embodiments, n is 1. In some embodiments, n is 3. In some embodiments, n is 5.

In some embodiments, $R^1$ is selected from $C_{1-3}$ alkyl, $C_{1-3}$ haloalkyl, $C_{2-4}$ alkenyl, and $C_{6-10}$ aryl. In some embodiments, $R^1$ is selected from $C_{1-3}$ alkyl and $C_{1-3}$ haloalkyl. In some embodiments, $R^1$ is $C_{6-10}$ aryl. In some embodiments, $R^2$ is selected from $C_{1-3}$ alkyl, $C_{1-3}$ haloalkyl, $C_{2-4}$ alkenyl, and $C_{6-10}$ aryl. In some embodiments, $R^2$ is selected from $C_{1-3}$ alkyl and $C_{1-3}$ haloalkyl. In some embodiments, $R^1$ is $C_{6-10}$ aryl. In some embodiments, $R^1$ is $C_{1-3}$ alkyl and $R^2$ is $C_{1-3}$ alkyl. In some embodiments, $R^1$ is $C_{6-10}$ aryl and $R^2$ is $C_{1-3}$ alkyl. In some embodiments, $R^1$ and $R^2$ together form $C_{1-3}$ alkylene.

In some embodiments, L is halogen. In some aspects of these embodiments, L is selected from Cl, Br, and F.

In some embodiments, L is $NR^{c1}R^{d1}$. In some aspects of these embodiments, $R^{c1}$ and $R^{d1}$ are independently selected from H, $C_{1-3}$ alkyl, $C_{1-3}$ haloalkyl, and $C_{3-10}$ cycloalkyl. In some embodiments, $R^{c1}$ is $C_{1-3}$ alkyl and $R^{d1}$ is H. In some embodiments, $R^{c1}$ is $C_{3-10}$ cycloalkyl and $R^{d1}$ is H. In some embodiments, $R^{c1}$ and $R^{d1}$ are each $C_{1-3}$ alkyl. In some embodiments, L is $NH_2$. In some embodiments, L is cyclohexylamine.

In some embodiments, n is 3, 4, or 5, any two L are each $NR^{c1}R^{d1}$, and any two $R^{c1}$ together form $C_{1-3}$ alkylene. In some embodiments, n is 3, 4, or 5, any two L are each $NR^{c1}R^{d1}$ and any two $R^{c1}$ together form $C_{3-10}$ cycloalkylene.

In some embodiments, any two L form a bidentate ligand selected from:

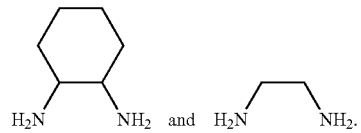

In some embodiments, L is $C_{2-12}$ alkene. In some aspects of these embodiments, L is selected from ethylene, propylene, butylene, cyclopropene, cyclobutene, cyclopentene, and cyclohexene.

In some embodiments, any two L together form a bidentate ligand which is from $C_{4-12}$ alkyldiene. In some aspects of these embodiments, the $C_{4-12}$ alkyldiene is selected from:

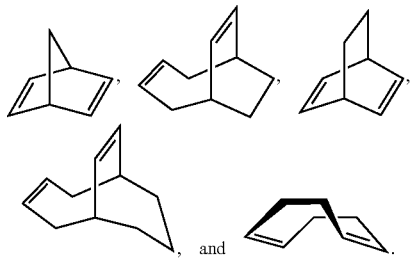

In some embodiments, L is $OR^{a1}$. In some aspects of these embodiments, L is OH. In other aspects of these embodiments, L is selected from methoxy, ethoxy, propoxy, and isopropoxy.

Typically bidentate groups are moderate leavings groups due to the two-step mechanism of ligand loss, but the resonance stabilization properties of alkenes or the trans effect of the sulfur-containing ligands (e.g., as required in Formula I) facilitate ring opening and subsequent loss of the bidentate ligand.

In some embodiments, L is $H_2O$. In some embodiments, L is selected from methanol, ethanol, propanol, and isopropanol.

In some embodiments, L is $NC-R^3$. In some embodiments, $R^3$ is selected from $C_{1-3}$ alkyl, $C_{1-3}$ haloalkyl, and $C_{6-10}$ aryl. In some embodiments, $R^3$ is $C_{1-3}$ alkyl. In some embodiments, $R^3$ is $C_{6-10}$ aryl. In some embodiments, L is selected from acetonitrile, acrylonitrile, and benzo nitrile.

In some embodiments, L is $P(R^{a1})_3$. In some embodiments, each $R^{a1}$ is independently selected from H, $C_{1-6}$ alkyl and $C_{6-10}$ aryl. In some embodiments, L is $P(R^{a1})_3$ and each $R^{a1}$ is $C_{1-6}$ alkyl. In some embodiments, L is $P(R^{a1})_3$ and each $R^{a1}$ is $C_{6-10}$ aryl. In some embodiments, L is selected from tris(4-methoxyphenyl)phosphine, tris(4-fluorophenyl)phosphine, (2,4,6-tri-tert-butylphenyl)phosphine, diphenyl(p-tolyl)phosphine, tri(p-tolyl)phosphine, tris(4-trifluoromethylphenyl)phosphine, triphenylphosphine and tri-tert-butylphosphine. In some embodiments, L is triphenylphosphine ($PPh_3$). In some embodiments, L is tri-tert-butylphosphine (P(t-Bu)$_3$).

In some embodiments, L is sulfoxide of formula $S(O)_2R^1R^2$, and $R^1$ and $R^2$ are as described herein. In some embodiments, L is a sulfoxide selected from dimethyl sulfoxide, dimethyl sulfoxide, methyl phenyl sulfoxide, diphenyl sulfoxide, p-tolyl sulfoxide, methyl p-tolyl sulfoxide, butyl sulfoxide, butyl methyl sulfoxide, and dodecyl methyl sulfoxide. In some embodiments, L is a dimethyl sulfoxide (DMSO).

In some embodiments, L is a sulfide of formula $SR^1R^2$, and $R^1$ and $R^2$ are as described herein. In some embodiments, L is selected from phenyl sulfide, methyl p-tolyl sulfide, ethyl phenyl sulfide, dimethyl sulfide, diethyl sulfide, di-n-butyl sulfide, and dioctyl sulfide. In some embodiments, L is dimethyl sulfide. In some embodiments, L is diethyl sulfide. In some embodiments, L is a sulfur-containing ligand selected from N-acetylcysteine, D-methionine and glutathione.

In some embodiments, L is 5-10 membered heteroaryl. In some embodiments, L is selected from imidazole, pyrazole, pyridine, pyrimidine, pyrazine, and pyridazine. In some embodiments, L is pyridine.

In some embodiments, any two L together form a bidentate ligand which is 12-16 membered fused heteroaryl. In some embodiments, the 12-16 membered fused heteroaryl has formula:

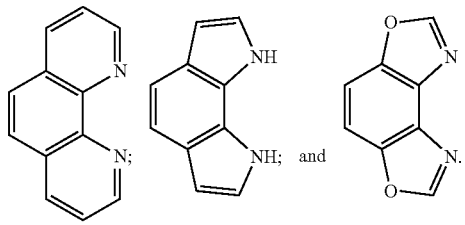

In some embodiments, any two L together form a bidentate ligand which is bis (5-10 membered heteroaryl). In some embodiments, the bis (5-10 membered heteroaryl) is selected from:

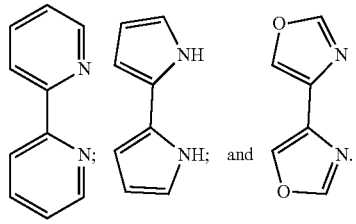

In some embodiments, the compound of Formula (I) does not contain a carboxy ligand (e.g., oxalate, succinate, malonate acetate). In some embodiments, the compound of Formula (I) does not contain a ligand that is perpendicular to the square plane of the Pt complex. In these embodiments, the compound does not contain a ligand which is 2-methylpyridine.

In some embodiments, the ligand L in the compound of Formula (I) is not rigid or bulky, because steric hindrance may interfere with the molecular rearrangements that occur during nucleophilic attack, thereby limiting cyanide anion's ability to access the platinum atom.

In some embodiments, n is 1, and L is selected from halogen and $NR^{c1}R^{d1}$.

In some embodiments, n is 3, and each L is independently selected from halogen, $S(O)_2R^1R^2$, and $SR^1R^2$. In some embodiments, n is 3, and each L is independently selected from halogen, $NR^{c1}R^{d1}$, and $S(O)_2R^1R^2$. In some embodiments, n is 3, and each L is independently selected from halogen, $NR^{c1}R^{d1}$, $P(R^{a1})_3$, and $S(O)_2R^1R^2$. In some embodiments, n is 3, and each L is independently selected from halogen, $NR^{c1}R^{d1}$, and $P(R^{a1})_3$. In some embodiments, n is 3, and each L is independently selected from halogen and $NR^{c1}R^{d1}$.

In some embodiments, the compound of Formula (I) is selected from:

(36)

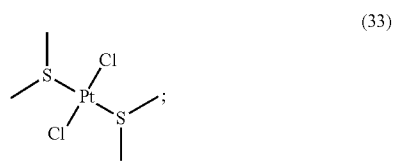

(33)

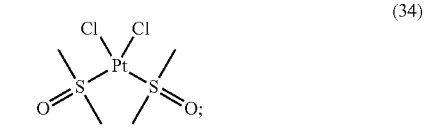

(34)

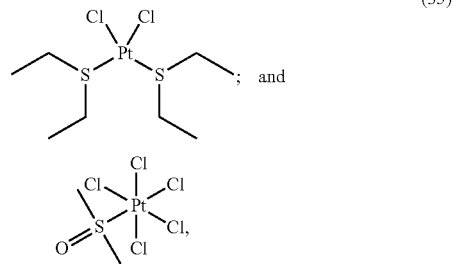

(35)

or a pharmaceutically acceptable salt thereof.

In some embodiments, the compound of Formula (I) is an adduct of a compound of Formula (II) and DMSO. In some aspects of these embodiments, the compound of Formula (I) is an adduct of hexachloroplatinate and DMSO.

In some embodiments, the compound of Formula (I) is:

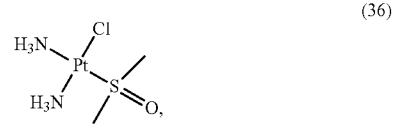

(36)

or a pharmaceutically acceptable salt thereof.

In some embodiments, the compound of Formula (I) is:

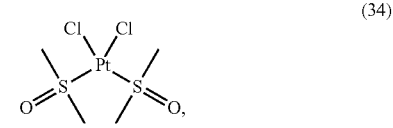

(34)

or a pharmaceutically acceptable salt thereof.

In some embodiments, the compound of Formula (I) is:

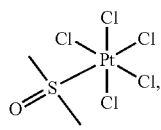

or a pharmaceutically acceptable salt thereof.

In some embodiments, the compound of Formula (I) is:

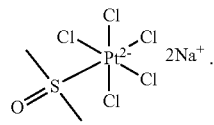

In some embodiments, the compound of Formula (I) is:

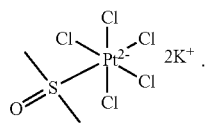

Without being bound to any particular theory, it is believed that the trans-directing effect of sulfur in the compound of Formula (I) affects the substitution kinetics of platinum complexes with the sulfur-containing ligands such as DMSO. A trans-directing ligand affects the lability of the ligand trans to itself and directs the positioning of an entering ligand (e.g., CN) to that position. For instance, complex 36 has two cis ammonia ligands, one chloride and one DMSO ligand, which is trans to one of the ammonia ligands. Ammonia ligands are extremely poor leaving groups. However, the potent trans-directing effect of sulfur in the DMSO ligand weakens the ammonia ligand bonded trans to its position. Thus in this configuration, upon nucleophilic attack of the complex by cyanide anion, the ammonia ligand (—NH$_3$) leaves first (See. e.g., Ref. 20).

In some embodiments, when the platinum complex of the present application contains a sulfur-containing ligand, the cyanide anion displaces an ammonia ligand or a halogen ligand (i.e., ammonia ligand or the halogen ligand is a leaving group). When an amine ligand and a halogen ligand are both present in the sulfur-containing complex, the cyanide anion may displace the amine ligand or the halogen ligand. In one example, the cyanide anion preferentially displaces the amine ligand. In another example, the cyanide anion preferentially displaces the halogen ligand. The order and rate with which a ligand is displaced by a cyanide anion may be based on the number of ligands already displaced by the cyanide and the kinetics of displacement of these ligands by associative substitution. In turn, associative substitution reactions are governed by factors including: (1) the nature of the metal (in this case platinum); (2) the charge or electrons to be donated by the nucleophile (in this case the cyanide anion), and (3) the characteristics of the ligands coordinated to the metal (the leaving group ligands).

In some embodiments, the present application provides a compound of formula (II):

or a pharmaceutically acceptable salt thereof, wherein:
each Hal is independently a halogen;
m is an integer selected from 0, 2, 3, and 4; and
Pt and L are as described herein for Formula (I).

In some embodiments, each Hal is selected from Cl, Br, and F. In some embodiments, each Hal is selected from Cl and Br. In some embodiments, one Hal is Cl and the other Hal is Br. In some embodiments, each Hal is Cl. In some embodiments, each Hal is Br.

In some embodiments, m is 0. In some embodiments, m is 2. In some embodiments, m is 4.

In some embodiments, each L is a ligand independently selected from halogen, NR$^{c1}$R$^{d1}$, NR$^{c1}$R$^{d1}$R$^{e1}$, C$_{2-12}$ alkene, NC—R$^3$, P(R$^{a1}$)$_3$, S(O)$_2$R$^1$R$^2$, SR$^1$R$^2$, and 5-10 membered heteroaryl; or
any two L together form a bidentate ligand selected from C$_{4-12}$ alkyldiene, 12-16 membered fused heteroaryl, and bis (5-10 membered heteroaryl);
each R$^{a1}$ is independently selected from H, C$_{1-6}$ alkyl, C$_{1-3}$ haloalkyl, C$_{2-4}$ alkenyl, C$_{2-4}$ alkynyl, and C$_{6-10}$ aryl;
each R$^{c1}$, R$^{d1}$, and R$^{e1}$ is independently selected from H, C$_{1-3}$ alkyl, C$_{1-3}$ haloalkyl, C$_{2-4}$ alkenyl, C$_{2-4}$ alkynyl, and C$_{3-10}$ cycloalkyl; or
any two R$^{c1}$ together form a group selected from C$_{1-3}$ alkylene, C$_{2-4}$ alkenylene, and C$_{3-10}$ cycloalkylene; and
R$^3$ is selected from C$_{1-3}$ alkyl, C$_{1-3}$ haloalkyl, C$_{2-4}$ alkenyl, C$_{2-4}$ alkynyl, and C$_{6-10}$ aryl.

In some embodiments, m is 2, and each L is independently selected from halogen, NR$^{c1}$R$^{d1}$, C$_{2-12}$ alkene, NC—R$^3$, P(R$^{a1}$)$_3$, S(O)$_2$R$^1$R$^2$, SR$^1$R$^2$, and 5-10 membered heteroaryl. In some embodiments, m is 2, and each L is independently selected from halogen, C$_{2-12}$ alkene, NC—R$^3$, P(R$^{a1}$)$_3$, S(O)$_2$R$^1$R$^2$, SR$^1$R$^2$, and 5-10 membered heteroaryl.

In some embodiments, m is 2, and each L is a ligand independently selected from halogen, NR$^{c1}$R$^{d1}$R$^{e1}$, C$_{2-12}$ alkene, NC—R$^3$, P(R$^{a1}$)$_3$, and 5-10 membered heteroaryl. In some embodiments, m is 2, and each L is a ligand independently selected from halogen, C$_{2-12}$ alkene, NC—R$^3$, P(R$^{a1}$)$_3$, and 5-10 membered heteroaryl. In some embodiments, m is 2, and each L is independently SR$^1$R$^2$. In some embodiments, m is 2, and each L is independently S(O)$_2$R$^1$R$^2$. In some embodiments, m is 2, and each L is independently selected from halogen and C$_{2-12}$ alkene. In some embodiments, m is 2, and two L together form a bidentate ligand which is C$_{4-12}$ alkyldiene. In some embodiments, m is 2, and two L together form a bidentate ligand which is 12-16 membered fused heteroaryl. In some embodiments, m is 2, and two L together form a bidentate ligand which is bis (5-10 membered heteroaryl). The C$_{4-12}$ alkyldiene, 12-16 membered fused heteroaryl, and bis (5-10 membered heteroaryl) bidentate ligands are described herein for Formula (I). In some embodiments, m is 2, and each L is independently P(R$^{a1}$)$_3$. In some embodiments, m is 2, and each L is independently NC—R$^3$. In some embodiments, m is 4, and each L is a halogen. In these embodiments, each L is selected from Cl and Br. In some embodiments, m is 4, and each L is independently selected from halogen and NR$^{c1}$R$^{d1}$.

In some embodiments, the compound of Formula (II) is selected from:
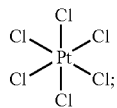 (3)
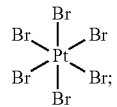 (6)
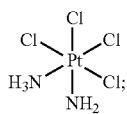 (5)
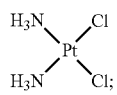 (7)
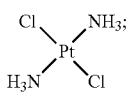 (8)
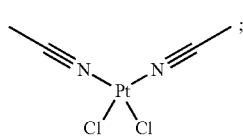 (10)
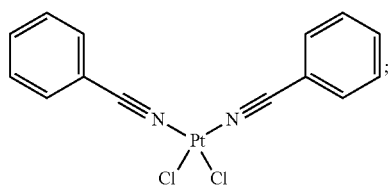 (11)
 (13)
 (12)
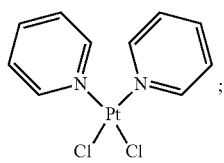 (20)
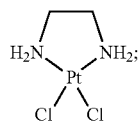 (21)
-continued
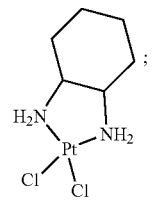 (22)
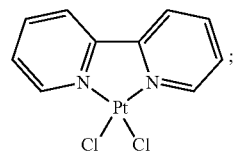 (23)
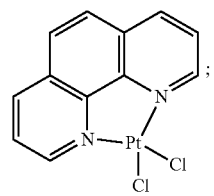 (24)
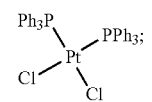 (27)
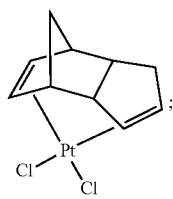 (29)
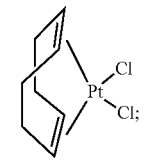 (30)
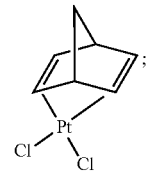 (31)
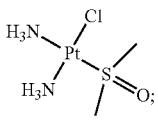 (36)
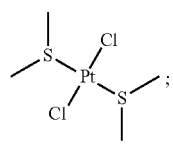 (33)

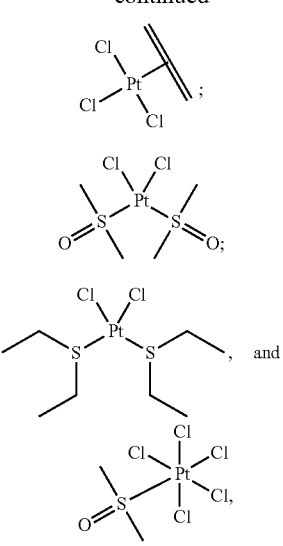

or a pharmaceutically acceptable salt thereof.

In some embodiments, the compound of Formula (II) is cisplatin (CAS Registry No. 15663-27-1), or a pharmaceutically acceptable salt thereof. In some embodiments, the compound of Formula (II) is not cisplatin.

In some embodiments, the compound of Formula (II) is $H_2PtCl_6$.

In some embodiments, the compound of Formula (II) is:

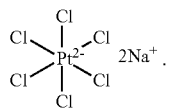

In some embodiments, the compound of Formula (II) is:

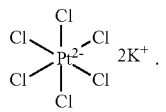

In some embodiments, the compound of the present application has fast CN substitution kinetics for at least one of the ligands, and is selectively reactive toward cyanide anion over any other biologically abundant nucleophile (e.g., sulfo, hydroxy and amino groups of proteins, RNA and DNA). In these embodiments, the compound rapidly and efficiently reacts with the cyanide but does not react with the biological nucleophiles such as DNA. This reactivity pattern makes the compound a strong cyanide antidote that is non-toxic to the subject. Therefore, the compound of the present application possesses the optimal balance of reactivity, efficacy and toxicity.

In some embodiments, a salt of a compound of Formulae (I) or (II) is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formulae I, II, or III include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formulae I, II, or III include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formulae (I) or (II), or pharmaceutically acceptable salts thereof, are substantially isolated.

Methods of Making Therapeutic Compounds

Compounds of Formulae (I) and (II), including salts thereof, can be prepared using known organic synthesis techniques and can be synthesized according to any of numerous possible synthetic routes. A person skilled in the art knows how to select and implement appropriate synthetic protocols, and appreciates that the processes described are not the exclusive means by which compounds provided herein may be synthesized, and that a broad repertoire of synthetic organic reactions is available to be potentially employed in synthesizing compounds provided herein.

Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

Methods of Use

In some embodiments, compounds described herein contain a positively charged platinum core and from 2 to 6 ligands, at least once of which is a leaving group. That is, the platinum core is amenable to a nucleophilic attack by a cyanide ion, whereby cyanide ion binds to the platinum atom and displaces the leaving group ligand. In some embodiments, each platinum complex is capable of binding from 1 to 6, from 1 to 5, from 1 to 4, or from 1 to 3 cyanide anions. That is, each platinum complex of the present application is capable of binding 1, 2, 3, 4, 5, or 6 cyanide anions.

Due to the ability of the platinum core to bind cyanide anion, the compound described herein may be used an antidote to cyanide poisoning. In some embodiments, the present application provides methods for treating or preventing cyanide poisoning, comprising administering to a subject in need thereof a therapeutically effective amount of a compound of Formula (I) or Formula (II), or a pharmaceutically acceptable salt thereof.

Because cyanide inhibits mitochondrial enzyme cytochrome c oxidase, cells of the organism poisoned with cyanide are unable to use oxygen to create ATP, the condition also known as cellular hypoxia. In some embodiments, the methods can include identifying a subject who has been exposed to cyanide. Subjects who are in need of treatment using a method or compound described herein can be identified by those of skill in the art, using known methods. Early symptoms of cyanide poisoning include headache, dizziness, fast heart rate, shortness of breath, and vomiting. These initial symptoms may be followed by seizures, slow heart rate, low blood pressure, loss of consciousness, cardiac arrest, and death. In case of a survival, consequences of cyanide poisoning may be long-term and may include chronic respiratory illnesses (e.g., chronic obstructive pulmonary disease (COPD), asthma, or pulmonary hypertension), blindness, damage and loss of function of vital organs (e.g., heart, lungs, kidneys, and brain), cognitive deficit, and cardiac, neurological, and metabolic dysfunction. In some embodiments, administration of the Pt-based compounds described herein protects from or induces rapid reversal of cyanide-induced pathophysiologic changes.

In one example, cyanide-caused metabolic dysfunction includes disrupted metabolism (e.g., decreased production) of bile acids and purine nucleobases, nucleosides and nucleotides. Some examples of bile acids include glycochenodeoxycholic acid, taurocholic acid, and taurochenodeoxycholic acid. Examples of purine nucleosides and nucleotides include inosine, deoxyadenosine, deoxyguanosine, adenosine, guanosine. Examples of purine nucleobases include purine, adenine, guanine, hypoxanthine, xanthine, theobromine, and uric acid. In another example, cyanide-caused metabolic dysfunction includes increased concentration of tricarboxylic acid (TCA) cycle metabolites as the cyanide causes their consumption to slow down. Examples of TCA cycle metabolites include α-ketoglutaric acid, succinic acid, fumaric acid, and malic acid.

In some embodiments, the cyanide poisoning in a subject may be caused by breathing smoke form a fire, exposure to insecticides, administration of medication nitroprusside, an industrial accident, or exposure to chemical warfare. Cyanide is readily absorbed through dermal, bronchial, and digestive routes, rapidly distributes to tissues throughout the body, and causes multi-organ toxicity, especially to organs having high demand for ATP such as brain and heart. Exposure to milligram amounts of the poison induces symptoms that appear within minutes of exposure. In some embodiments, any of the methods of use mentioned herein do not include the use cisplatin or carboplatin.

In some embodiments, the antidote activity ($EC_{100}$) of the compounds of the present application is from about 5 μM to about 2000 from about 10 μM to about 1000 μM, from about 25 μM to about 1000 μM, from about 50 μM to about 1000 μM, from about 50 μM to about 500 of from about 50 μM to about 250 μM.

In some embodiments, a compound of the present application is a cyanide antidote at a dose from about 1 mg/kg to about 500 mg/kg, from about 5 mg/kg to about 400 mg/kg, from about 10 mg/kg to about 300 mg/kg, or from about 5 mg/kg to about 250 mg/kg. In some embodiments, a compound of the present application has a lowest lethal dose ($LD_{Lo}$) from about 10 mg/kg to about 5000 mg/kg, from about 50 mg/kg to about 2000 mg/kg, from about 100 mg/kg to about 1000 mg/kg, from about 150 mg/kg to about 1000 mg/kg, from about 180 mg/kg to about 1000 mg/kg, from about 250 mg/kg to about 1000 mg/kg, or from about 500 mg/kg to about 1000 mg/kg.

In some embodiments, the compounds of Formula (I) or Formula (II) may be used is cyanide sensing (e.g., in a sensor for cyanide anions). When compound of Formula (I) or Formula (II) binds cyanide, it turns into a different chemical compound. Thus, the difference is physical properties between the parent compound and the CN adduct (e.g., δ in UV-vis or IR absorption) may be measured and used to determine the presence of cyanide.

Combinations

In another general aspect, the compound of any one of Formulae described herein may be administered to the subject in combination with an additional therapeutic agent. In some embodiments, the additional therapeutic agent is useful in treating and/or preventing cyanide poisoning. Examples of such additional therapeutic agents include cyanide antidotes. In some embodiments, the additional therapeutic agent is selected from hydroxocobalamin, methemoglobin, riboflavin, methotrexate, sulfanegen, 3-mercaptopyruvic acid (3-MP), amyl nitrite, sodium nitrite, sodium thiosulfate, 4-dimethylaminophenol (4-DMAP), dicobalt edetate, and glucose. In some embodiments, the additional therapeutic agent is oxygen therapy.

In some embodiments, the compound of any one of Formulae described herein and the additional therapeutic agent may be administered to the subject simultaneously (e.g., in the same dosage form or in separate dosage forms), or consecutively (e.g., the compound of any one of Formulae described herein may be administered before or after the additional therapeutic agent). Any one of the dosage forms and routes described herein for the administration of a compound of any one of the Formulae (I)-(III) may be used for administering the additional therapeutic agent to the subject. The dosages and routes of administration of a combination therapy are well within the judgement of treating physician (e.g., emergency room doctor or critical care physician).

Kits

The present invention also includes kits (e.g., pharmaceutical kits) useful, for example, in treating or prevention of cyanide poisoning referred to herein, which include one or more containers containing a pharmaceutical composition comprising a therapeutically effective amount of a compound of Formula (I) or Formula (II), or a pharmaceutically acceptable salt thereof. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit may optionally include an additional therapeutic agent, such as a cyanide antidote, in any one of amounts and dosage forms described herein.

In some embodiments, the compound of Formula (II) may be included in the kit along with a container with dimethyl sulfoxide (DMSO), and optionally instructions to combine the compound of Formula (II) and DMSO. Such kit may also include containers with one or more pharmaceutically acceptable carriers (e.g., saline), additional instructions and guidelines for administration, and other conventional kit components mentioned herein. In some embodiments, the compound of Formula (II) is converted into a cyanide antidote agent by solvation in DMSO. In some embodiments, the compound of Formula (II) is cisplatin, or a pharmaceutically acceptable salt thereof, and the cyanide antidote agent formed by solvation in DMSO is a compound (36). Although the DMSO adduct form of cisplatin undermines the drug's utility as a chemotherapeutic drug, the decreased toxicity is a beneficial aspect for its use as a cyanide antidote because it reduces toxicity while improving interaction with cyanide. In some embodiments, the compound of Formula (II) is hexachloroplatinate (compound 3), or a pharmaceutically acceptable salt thereof, and the cyanide antidote agent formed by solvation in DMSO is $PtCl_5$ (DMSO), or a salt pharmaceutically acceptable salt thereof.

Pharmaceutical Compositions

The present application also provides pharmaceutical compositions comprising an effective amount of a compound of any one of Formulae (I) or (II) disclosed herein, or a pharmaceutically acceptable salt thereof; and a pharmaceutically acceptable carrier. The pharmaceutical composition may also comprise any one of the additional therapeutic agents described herein (e.g., hydroxocobalamin, riboflavin, methotrexate). In certain embodiments, the application also provides pharmaceutical compositions and dosage forms comprising any one the additional therapeutic agents described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up from the suitable pharmaceutically acceptable excipients. The contemplated compositions may contain 0.001%400% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endosinusial, endotracheal, enteral, interstitial, intra-abdominal, intra-arterial, intrabronchial, intraosseous (e.g., infusion), intracoronary, intradermal, intraductal, intraduodenal, intradural, intraepidermal, intraesophageal, intragastric, intragingival, intraileal, intralymphatic, intramedullary, intrameningeal, intramuscular, intranasal, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, ampules for injection, and in liposomes, and may be prepared by any methods well known in the art of pharmacy. See, for example, Remington: The Science and Practice of Pharmacy, Lippincott Williams & Wilkins, Baltimore, Md. (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration may be presented as discrete units such as capsules, sachets, granules or tablets, or ampules for injection, each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing oral suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous (e.g., DMSO) sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol or in dimethyl sulfoxide (DMSO). Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol*, 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Dosages and Regimens

In the pharmaceutical compositions of the present application, a compound of any one of Formulae (I) or (II) is present in an effective amount (e.g., a therapeutically effective amount).

Effective doses may vary, depending on the severity of cyanide poisoning, the route of administration, the sex, age and general health condition of the subject, excipient usage, the possibility of co-usage with other therapeutic treatments such as use of other agents and the judgment of the treating physician.

In some embodiments, an effective amount of a compound of any one of Formulae (I)-(II) can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a compound of any one of Formulae (I)-(III) is about 0.1 mg/kg, about 0.5 mg/kg, about 1 mg/kg, about 2 mg/kg, or about 5 mg/kg.

In some embodiments, an effective amount of a compound of any one of Formulae (I)-(II) can range, for example, from about 10 mg/dose to 1000 mg/dose (e.g., 50 mg/dose, 100 mg/dose, 200 mg/dose, 300 mg/dose, 400 mg/dose, or 500 mg/dose).

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

Definitions

At various places in the present specification, substituents of compounds of the present application are disclosed in groups or in ranges. It is specifically intended that various embodiments of the present application include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the term "about" means "approximately" (e.g., plus or minus approximately 10% of the indicated value).

As used herein, the term "compound" as used herein is meant to include all stereoisomers, geometric isomers, tautomers, and isotopes of the structures named or depicted. Compounds herein identified by name or structure as one particular tautomeric form are intended to include other tautomeric forms unless otherwise specified.

As used herein, the term "tautomer" refers to compounds which are capable of existing in a state of equilibrium between two isomeric forms. Such compounds may differ in the bond connecting two atoms or groups and the position of these atoms or groups in the compound.

As used herein, the term "isomer" refers to structural, geometric and stereo isomers. As the compound of the present application may have one or more chiral centers, it is capable of existing in enantiomeric forms.

Throughout the definitions, the term "$C_{n-m}$" indicates a range which includes the endpoints, wherein n and m are integers and indicate the number of carbon atoms. Examples include $C_{1-4}$, $C_{1-6}$, and the like.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain (linear) or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkylene" means a bivalent saturated branched, or straight chain (linear) chemical group containing only carbon and hydrogen atoms, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, the term "$C_{n-m}$ alkyldiene" refers to alkanes and alkyl groups having two double bonds in the carbon chain. Non-limiting examples of alkyldienes include 1,3-butadiene, isoprene, cyclooctadiene, dicyclopentadiene, and norbornadiene.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms. The term "$C_{n-m}$ alkenylene" refers to a divalent alkenyl group.

As used herein, the term "alkene" includes an unsaturated hydrocarbon that contains at least one carbon-carbon double bond. An alkene compound may have chemical formula $C_nH_{2n}$, where n is an integer from 2 to 20. Non-limiting examples of alkene compounds include ethylene, 2-propylene, 2-butylene, 2-octene.

As used herein, "$C_{n-m}$ alkynyl" means a straight or branched chain chemical group containing only carbon and hydrogen, containing n to m carbon atoms and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms). The term "$C_{n-m}$ alkynylene" refers to a divalent alkynyl group.

As used herein, "halo" or "halogen" refers to a halogen atom such as F, Cl, Br, or I. In some embodiments, a halo is F, Cl, or Br. In other embodiments, halo is F, Cl, or I. In other embodiments, halo is F, I, or Br.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic saturated or unsaturated cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the non-aromatic cyclic hydrocarbon, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, or 12 ring-forming atoms. In some embodiments, the cycloalkyl is a 3-12 membered monocyclic or bicyclic cycloalkyl. In some embodiments, the cycloalkyl is a $C_{3-7}$ monocyclic cycloalkyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cyclooctyl, cyclooctenyl, and the like. In some embodiments, cycloalkyl is cyclopropyl, cyclobutyl, cyclopentyl, cyclohexyl, cyclooctyl, or cyclooctenyl. In some embodiments, the cycloalkyl is a cyclooctenyl ring fused with 1 or 2 benzene rings. In some embodiments, the cycloalkyl is a 3-8 membered or 3-7 membered monocyclic cycloalkyl group (e.g., $C_{3-8}$ or $C_{3-7}$ cycloalkyl). In some embodiments, the cycloalkyl is a 8-12-membered bicyclic cycloalkyl. In some embodiments, the cycloalkyl is a 8-16-membered bicyclic or tricyclic cycloalkyl (e.g., $C_{8-16}$ cycloalkyl). In some embodiments, the cycloalkyl is unsaturated cyclic hydrocarbon group (i.e., the cycloalkyl contains at least one double bond). The term "cycloalkylene" refers to a divalent cycloalkyl group, such as cyclohexylene.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 membered monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered heteroaryls are pyridyl, pyrazinyl, pyrimidinyl, triazinyl and pyridazinyl. The term "heteroarylene" refers to a divalent heteroaryl linking group.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl. The term "arylene" refers to a divalent aryl linking group. In some embodiments, the term "aryl" includes optionally substituted aryl groups. The optional substituents include $C_{1-3}$ alkyl, halogen, $C_{1-3}$ haloalkyl, $C_{2-4}$ alkenyl, $C_{2-4}$ alkynyl, OH, CN, $NO_2$, $C_{1-3}$ alkoxy, $C_{1-3}$ haloalkoxy, $NH_2$, $C_{1-3}$ alkylamino, and di($C_{1-3}$ alkyl)amino.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the terms "maximum safe dosage", "maximum tolerated dosage" or "maximum recommended therapeutic dosage" indicate the highest amount of a therapeutic agent that can be given that minimizes complications or side effects to a patient while maintaining its efficacy as a treatment. Such a dose can be adjusted to consider the patient's overall heath and any extenuating factors that could hamper the patient's recovery.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

As used herein, the term "cyanide poisoning" includes cyanide-caused conditions such as cellular hypoxia and related symptoms including headache, dizziness, fast heart rate, shortness of breath, and vomiting. The term "cyanide poisoning" also includes conditions such as cyanide-caused slow heart rate, low blood pressure, loss of consciousness, cardiac arrest, and death. In case of survival of a poisoned subject, the term also includes cyanide-caused long-term conditions such as chronic respiratory illness, blindness, cognitive deficit, and pathophysiologic changes such as cardiac, neurological, and metabolic dysfunction.

EXAMPLES

Experimental Model and Subject Details

Zebrafish.

Animals were maintained and embryos were obtained according to standard fish husbandry protocols in accordance with the Massachusetts General Hospital Institutional Animal Care and Use Committee. Zebrafish embryos (Ekkwill strain) were grown at 28° C. in HEPES buffered Tubingen E3 medium and assayed at 6 d.p.f.

Mice.

All studies were carried out according to NIH Guidelines for the Care and Use of Laboratory Animals and approved by the Veterans Administration San Diego Healthcare System's Institutional Animal Care and Use Committee. C57/BL6J male (Jackson Laboratories) mice weighing 20-25 g were used and were fed ad libitum Teklad #7001.

Rabbits.

The protocol was reviewed and approved by the University of California Irvine (UCI) Institutional Animal Care and Use Committee (IACUC). Pathogen-free New Zealand White rabbits (Western Oregon Rabbit Supply), weighing 3.5-4.5 kg were used in this study.

Tissue Culture Cells.

H1975 non-small cell cancer cells were grown in RPMI-1640 Medium supplemented with 10% FBS, 2 mM L-glutamine, 1 mM sodium pyruvate, 100 IU/ml penicillin and 100 µg/ml streptomycin.

Method Details

Preparation of Hexachloroplatinate (HCP).

To 120 mg sodium HCP, were added 120 µL DMSO. The tube was placed in a 95° C. water bath for a few minutes. The tube was vortexed for 2 minutes. Next 1.26 mL of the $Ca^{2+}$, $Mg^{2+}$-free PBS solution (at 95° C.) was added to the tube. The solution was next vortexed for 2 minutes. This solution was delivered IM.

In Vivo SAR Studies.

The assay was carried out on 6 d.p.f. larval zebrafish loaded in 96-well plates containing HEPES buffered Tubingen E3 medium (n=5 per well). Compounds were screened using a 12 point dose response analysis 0.4-1000 µM. Potassium cyanide was added at a dose of 100 µM which induces 100% death within 1 hour in controls animals. Following the addition of cyanide the plates were sealed with adhesive PCR plate foil and incubated at 28° C. The lowest effective dose to rescue 100% of larvae ($EC_{100}$) was reported 4 hours post treatment. For assessment of compound toxicity, larvae were treated for 24 hours with compounds and viability was assessed by observing heart rate and response to touch as previously describe. The dose that causes 100% lethality was reported ($LD_{100}$). All compounds were purchased from Sigma-Aldrich or Abcam. Complex 36 was prepared as previously described and its structure was confirmed by mass spectrometry (Ref 12). In the zebrafish assay, each dose of each drug was tested on 5 larvae and these experiments were repeated on 5 separate days.

UV-VIS Spectral Assay.

Cisplatin was dissolved in PBS (1 mM), DMSO (1 M), $H_2O$ (1 mM) or DMF (1 mM) and heated for several hours to generate the stock solution at the concentration indicated in parentheses. Subsequently the DMSO stock was diluted to 1 mM in PBS or $H_2O$. For dose response experiments, from a stock solution of 1M KCN in PBS or $H_2O$, a cyanide concentration curve from 1-200 mM was generated in PBS or $H_2O$. The reaction was incubated for 30 minute and the absorbance read over the UV-VIS spectrum on a NanoDrop (Thermo Scientific). For time course experiments, 1 mM complex was reacted with 5 mM KCN and the absorbance was measured every 1 minute for 5 minutes followed by every 5 minutes for 30 minutes. To create a polar aprotic environment, DMF was used as the solvent and assay buffer. All reactions were blanked to a solution of complex only.

Cytotoxicity Assay.

Cell viability was evaluated in H1975 cells, a cisplatin responsive non-small cell lung cancer line. Cells were plated into 96-well plates. When the plates reached 80% confluency, the cells were treated with the indicated compounds for 72 hours. The compounds were dissolved in DMSO or PBS and tested at doses at 0, 3, 10, 30 and 300 µM (eight wells per dose). Viability was assayed using the CellTiter-Glo Luminescent Cell Viability Assay (Promega) by gently removing the media prior to adding CellTiter-Glo reagent to the wells. Three biological replicates were performed.

Western Blot.

Cells were treated for 24 hours then lysed in NP-40 lysis buffer [50 mM Tris/HCl, pH 8.0, 150 mM NaCl, 1% NP-40, complete protease inhibitor tablets (Sigma-Aldrich) and PhosStop phosphatase inhibitor tablets (Roche)]. Lysates were ran on NuPAGE Novex 4-12% Bis-Tris Protein Gels (Invitrogen) and transferred to PVDF membranes. The membranes were blocked with 5% BSA for 1 hour at room temperature and probed with antibodies to phospho-p38 MAPK, p38 MAPK and β-actin overnight at 4° C. Three biological replicates were performed.

Mass Spectrometry.

The cisplatin-DMSO solution (100 mM) was generated by adding 15 mg cisplatin into 500 µl of DMSO (warmed to 95° C.). The solution was incubated in the dark for 1 hour. The hexachloroplatinate-DMSO solution (100 mM) was generated by adding 28 mg hexachloroplatinate into 500 µl of DMSO (warmed to 95° C.). The solution was incubated in the dark for 1 hour. Next, a solution of 1M KCN or $K^{13}C^{15}N$ was prepared in water that was adjusted to pH 7.4 with NaOH. Equal volumes of the platinum complexes and the cyanide solution were then combined, vortexed and incubated. The resulting mixture was diluted 10-fold with HPLC-grade methanol and then infused directly into an Agilent 6550 iFunnel Q-TOF Mass Spectrometer equipped with a dual AJS-ESI source at 10 µl/min. The source parameters for acquisition were set as: drying gas temperature and flow was 250° C. and 14 L/min respectively; nebulizer was set at 35 psig; sheath gas temperature and flow were 350° C. and 11 L/min respectively; Vcap and nozzle voltage were at 1500V and 2000V. The MS-only full scan and/or targeted MS/MS scan in positive mode was acquired through Agilent MassHunter Workstation LC/MS Data Acquisition software (version B.05.01). The mass range of TOF spectra was 70-1700 m/z and the acquisition rate was 1 spectra/sec. The reference mass of 121.050873 and 922.009798 was selected for mass correction. The acquired Q-TOF LC/MS data was analyzed with the Agilent MassHunter Workstation Qualitative Analysis software (version B.06.00) for peak identification. To further confirm the structure of identified compounds, the isotope distribution of the observed compound spectra was compared with predicted spectra generated using an Isotope Distribution Calculator and Mass Spec Plotter.

Mouse Cyanide Inhalation Model.

Mice were placed in an acrylic glass chamber and anesthetized by injecting isoflurane into the chamber (2% v/v).

The mice become anesthetized within 1-2 min, but 5 min are allowed to be sure they are in a homeostatic state before being cyanide exposure. Hydrogen cyanide is generated by injecting 0.1 M KCN into a beaker of 1 M sulfuric acid. Mice are exposed to cyanide gas for 15 min in gas chamber, removed from the chamber, injected with antidote, and re-exposed to cyanide gas for an additional 25 min. The antidotes are prepared in DMSO, diluted 10 fold in saline and injected IP. The animals are anesthetized with isoflurane throughout the cyanide exposure period and all surviving mice are euthanized at the end of the experiment. This model has been previously described (Ref 9).

Rabbit Cyanide Infusion Model.

Animals were anesthetized with an intramuscular injection of ketamine HCl 50 mg/kg (Ketaject, Phoenix Pharmaceutical Inc., St. Joseph, Mich.) and xylazine 5 mg/kg (Anased, Lloyed Laboratories, Shenandoah, Iowa). After the injection, a 23 gauge, 1 inch catheter was placed in the animal's marginal ear vein to administer continuous intravenous anesthesia with ketamine/xylazine. The depth of anesthesia was evaluated by monitoring the animals' physical reflexes and heart rate. Animals were intubated with a 3.0 cuffed endotracheal tube secured by a gauze tie; they were mechanically ventilated (dual phase control respirator, model 32A4BEPM-5R, Harvard Apparatus, Chicago, Ill.) at a rate of 20 respirations per minute, a tidal volume of 50 cc, and FiO2 of 100%. A pulse oximeter (Biox 3700 Pulse Oximeter, Ohmeda, Boulder, Colo.) with a probe was placed on the tongue to measure SpO2 and heart rate. Sodium cyanide, 10 mg in 60 cc normal saline, was infused continuously intravenously at a rate of 1 cc/min. Inspired oxygen remained at 100% throughout the experiment. At the end of infusion, antidote compounds were given IV and animals were monitored for an additional 90 minutes. The effects of cyanide toxicity and reversal of toxicity with antidotes were observed in real time using optical spectroscopy. Subsequently, the animals were euthanized with an intravenous injection of Euthasol (1.0 cc, Euthasol, Virbac AH, Inc. Fort Worth, Tex.). This model has been previously described (Ref. 7).

In Vivo Optical Spectroscopy.

The details of DOS and CWNIRS methodology have been previously described (FIG. 7). Briefly, DOS measurements were obtained through a fiber-optic probe placed on the shaved surface of the right inner thigh of the rabbit. The broadband DOS system combines multi-frequency domain photon migration with time-independent near infrared spectroscopy to accurately measure bulk tissue absorption and scattering spectra. Tissue concentrations of oxyhemoglobin, deoxyhemoglobin and cytochrome c redox state (ratio of oxidized to reduced cytochrome c) were calculated by a linear least squares fit of the wavelength-dependent extinction coefficient spectra of each chromophore. CWNIRS penetrates more deeply into tissues than DOS therefore was used to assess oxy- and deoxyhemoglobin effects of cyanide toxicity in the central nervous system. The CWNIRS system consists of a light source (HL 2000, Ocean Optics, FL), a CCD spectrometer (USB4000, Ocean Optics, FL), and customized optical fiber guides. Continuous wave near infrared light was delivered to the rabbit brain using a fiber optic probe (9 mm source-detector separation), and transmitted light intensities at five wavelengths (732, 758, 805, 840, 880 nm) were measured using the CCD spectrometer every second. We quantified changes in oxy- and deoxyhemoglobin concentrations throughout the experiment using a modified Beer-Lamberts' law and those changes are displayed in real time using Labview software (Labview 7.1, National Instrument, TX).

Quantification and Statistical Analysis.

Statistical parameters are reported in Figure Legends or in Method Details. In the zebrafish assay, each dose of each drug was tested on 5 larvae and these experiments were repeated on 5 separate days. Cell viability experiments were tested three separate times with error bars indicating the SD of 8 wells from one of the three replicates. The Western blot experiments were performed on 3 biological replicates. The murine cyanide inhalation model used 6 mice per treatment group. The rabbit cyanide infusion model used 5 rabbits per treatment group.

Rabbits Cyanide Model.

Pathogen-free male and female New Zealand White rabbits (Western Oregon Rabbit Supply) weighing 3.5-4.5 kg were used. All animals were anesthetized with ketamine and xylazine, intubated, and ventilated at a respiratory rate of 20 to 22 breaths/min, a tidal volume of 60 cc, and fraction of inspired oxygen (FiO$_2$) of 100%. Arterial and venous blood samples were drawn at the indicated time points. Rabbits were monitored for cyanide poisoning in real time using standard hemodynamics, gas exchange measures, and optical technologies including continuous wave near infrared spectroscopy diffuse optical spectroscopy as previously described. A lethal cyanide dose was achieved by intravenous administration of 22-26 mg sodium cyanide in 60 mL of saline at 1 cc/min (0.33 mg/min). The 100% O$_2$ supply was switched to atmospheric air after 30 minutes of CN infusion and the respiratory rate on the ventilator was reduced down to 18-20 breaths/min. When the blood pressure dropped below 40-58 mmHg, antidote or placebo was administered (IM into the right front limb muscle) and cyanide was continued for another 30 minutes. This results in 80% lethality unless the antidote is effective. Animals that survive are monitored for an additional 160 minutes. All methods were carried out in accordance with the regulations and guidelines of the Animal Welfare Act and the American Association for Accreditation of Laboratory Animal Care. All experimental protocols were approved by the IACUC committee at UC Irvine.

Swine Cyanide Model.

Female Yorkshire swine (Sus scrofa) (Oak Hill Genetics, Ewing, Ill.) weighing 45-55 kg were used for this study. Anesthesia is induced with IM administration of 10-20 mg/kg ketamine (MWI, Boise, Id.) and isoflurane (MWI, Boise, Id.) via nosecone. Following induction, animals are intubated with an 8.0 cuffed endotracheal tube (Teleflex, Morrisville, N.C.), and peripheral venous access obtained. Sedation is maintained using the Drager Fabius GS anesthesia machine (Drager, Houston, Tex.) with 1-3% isoflurane and 0.4 FiO$_2$. Tidal volume is set at 8 ml/kg and a respiratory rate 16-20 breaths per minute, adjusting the minute volume to maintain an end tidal CO$_2$ of 35-45 mmHg. A 7.5 ml/kg bolus of 0.9% saline (B. Braun, Bethlehem, Pa.) is given prior to central line placement. The external jugular and femoral artery are visualized using the M9 ultrasound system (Mindray, Mahwah, N.J.) and central venous and arterial access obtained. The Drager Infinity Delta Monitor (Drager, Houston, Tex.) monitors and records pulse oximetry, body temperature, invasive blood pressure, and ECG throughout the experiment. Invasive hemodynamic variables are measured via pulmonary artery catheterization using an eight-French Swan Ganz CCOmbo catheter and the Edwards Vigilance II monitor (Edwards Lifesciences, Irvine, Calif.). Once vascular access is obtained a one-time bolus of heparin (100 units/kg) is administered IV. Mechanical ventilation is then terminated, allowing the animal to breathe spontaneously and isoflurane as well as $FiO_2$ are weaned to 0.8-1% and 0.21, respectively.

Following a 10-minute acclimation period, animals were randomized into one of two treatment groups; IM HCP or vehicle control. Potassium cyanide (Sigma Aldrich, St. Louis, Mo.) diluted in saline (B. Braun, Bethlehem, Pa.) is delivered via continuous infusion into the right jugular vein until 5 minutes after apnea occurs. At this point, animals are treated with either HCP or vehicle control injected into the left gluteal muscle and the cyanide infusion is terminated. Following treatment animals are observed continuously for 90 minutes or until death, defined as a mean arterial pressure of less than 20 for 10 minutes. At the end of the study all animals are euthanized with an intravenous administration of 100 mg/kg sodium pentobarbital. All methods were carried out in accordance with the regulations and guidelines of the Animal Welfare Act and the American Association for Accreditation of Laboratory Animal Care. All experimental protocols were approved by the IACUC committee at the University of Colorado.

Pharmacokinetics of PtCN and PtCl Species.

To generate standard curves for the observed chloroplatinate and cyanoplatinate species, $K_2PtCl_4$, $Na_2PtCl_6.6H_2O$ and $K_2Pt(CN)_4$ standards (Sigma Aldrich) were dissolved in normal saline to generate 10 mM stock solutions. A hexachloroplatinate-DMSO (HCP-DMSO) solution (10 mM) was prepared by adding 5.6 mg of $Na_2PtCl_6.6H_2O$ into 1 mL of 95° C. DMSO followed by incubation in the dark for one hour. A solution of 1M potassium cyanide (pH 7.4 adjusted with sodium hydroxide) was prepared and then equal volumes of the HCP-DMSO and potassium cyanide solutions were combined, vortexed, and incubated in order to generate the cyanoplatinum complexes. Calibration standards with concentrations ranging from 0.00095 µM to 1000 µM were generated by spiking 2 µL of 10 mM solution into 18 µL of pooled plasma followed by serial dilutions in pooled plasma. The prepared calibration samples (10 µL) were deproteinized using 90 µL of 75:25 methanol:acetonitrile with isotopically labeled internal standards (phenylalanine d8 and valine d8). Samples were vortexed for 5 seconds and then subjected to centrifugation (14000 rpm, 20 minutes, 4° C.). Supernatants were transferred to glass autosampler vials with 300 µL inserts for analysis. Experimental samples were aliquoted (10 µL) and prepared using the same sample preparation workflow.

LC-MS data was acquired using a Hilic Chromatography on a 2.1×150×3.5 µm Atlantis HILIC column (Waters, Milford, Mass.). The chromatography system was an Agilent 1200 series LC with a CTC PAL Autosampler. Mobile phase A consisted of 10 mM ammonium formate in water with 0.1% formic acid, and mobile phase B consisted of 100% acetonitrile, with 0.1% formic acid (all components were Optima LC-MS grade, Fisher Scientific, Hampton, N.H.). The injection volume was 10 µL. Initial mobile phase conditions were 5% mobile phase A, 95% mobile phase B followed by a constant gradient to 60% mobile phase A, 40% mobile phase B over 10 minutes. The column was then re-equilibrated to initial mobile phase conditions over 20 minutes. The chromatography system was coupled to an Applied Biosciences/Sciex 4000 QTRAP mass spectrometer with an electrospray ionization source run in negative mode. MRM transitions were optimized for each species on the LC-MS system using Analyst Software (Sciex, Framingham, Mass.). Following optimization, calibration standards were run to generate a standard curve for each species. Next, experimental samples were run and signals for each PtCl and PtCN species were compared to the calibration curve in order to determine their absolute concentration.

Targeted Metabolomics.

Metabolites were measured in rabbit and pig serum using adapted LC-MS methods as previously developed. In this method, 30 µL aliquots were deproteinized using a 75:25 methanol:acetonitrile solution with isotopically labeled internal standards (citrulline D7, 10 µM, inosine $^{15}N_4$, 25 µM, phenylalanine D8, 10 µM, and thymine d4 25 µM). Following vortexing (5 seconds) and centrifugation (14000 rpm, 20 minutes, 4° C.), the supernatants were transferred to glass autosampler vials with 300 µL inserts for analysis.

LC-MS data was acquired using HILIC chromatography on a 2.1×100 mm×3.5 µm)(Bridge Amide column (Waters, Milford, Mass.) in negative ion mode. The chromatography system was an Agilent 1290 infinity HPLC coupled to an Agilent 6490 triple quadrupole mass spectrometer with an electrospray ionization source. Mobile phase A was 95:5 (v/v) water:acetonitrile (Fisher Scientific, Hampton, N.H.) with 20 mM ammonium acetate (Sigma-Aldrich, St. Louis, Mo.) and 20 mM ammonium hydroxide (Sigma-Aldrich, St. Louis, Mo.) (pH 9.5). Mobile phase B was 100% acetonitrile (Fisher Scientific, Hampton, N.H.). Injection volume was 5 µL. The mass spectrometry settings were: sheath gas temperature 400° C., sheath gas flow 12 L/min, drying gas temperature 290° C., drying gas flow 15 L/min, capillary voltage 4000V, nozzle pressure 30 psi, nozzle voltage 500V, and delta EMV 200V.

LC-MS data was quantified using Agilent MassHunter Quantitative Analysis software. All metabolite peaks were manually reviewed for peak quality in a blinded manner. Pooled plasma was interspersed throughout the run at regular intervals in order to monitor temporal drift in mass spectrometry performance. Metabolites were normalized to the baseline sample acquired for each animal on a metabolite-by-metabolite basis.

Murine Toxicity Study.

Male (n=8) and female (n=8) CD-1 mice (Envigo, Indianapolis, Ind.) age 3-4 weeks with weight ranges of 18-20 g were used for this study. Studies were performed at the Purdue Translational Pharmacology and Clinical Veterinary Pathology Laboratories which have IACUC approval to conduct toxicity studies. HCP was administered by IM injection in 50 µL of HCP solution (10% DMSO in $Ca^{2+}$ and $Mg^{2+}$-free PBS) into the gastrocnemius muscle. Blood was drawn 4 days post HCP injection (200 mg/kg IM) for conducting a Comprehensive Metabolite Panel and Complete Blood Count Panel. At the end of the study, the animals were humanely euthanized following the PHS Policy on the Human Care and Use of Animals, Guide for the Use and Care of Laboratory Animals. All major organs were harvested and subjected to histological analysis by a trained pathologist. All methods were carried out in accordance with the regulations and guidelines of the Animal Welfare Act and the American Association for Accreditation of Laboratory Animal Care. All experimental protocols were approved by the IACUC committee at Purdue University.

Statistics.

For the rabbit and pig data, significance was assessed using paired t-tests to compare the peak areas of baseline (pre-cyanide infusion) samples to end of the cyanide infusion samples. In both models, metabolite differences were then compared in baseline samples versus endpoint samples in order to demonstrate amelioration and a trend towards normalization by the experimental endpoint. To determine the percent change from baseline, we normalized metabolite levels in animals treated with cyanide to the value of their baseline (pre-cyanide infusion) peak area on a metabolite by metabolite basis, and then calculated the mean and standard error of the mean. In mice, the results of the Comprehensive Metabolite and Complete Blood Count Panels were compared between mice treated with HCP and mice treated with normal saline using Student's t-tests. Males and females were also compared separately to determine if gender specific changes had occurred.

Example 1—Platinum Complexes Act as Antidotes to Cyanide Poisoning by Binding the Cyanide Anion Upon exposure to cyanide, zebrafish larvae develop stereotypic dose-dependent cyanide pathologies including slow heart rate, deficits in standard neurobehavioral responses, and ultimately death. A dose of 100 µM of cyanide was used which kills zebrafish is less than 1 hour. Zebrafish larvae were treated with cisplatin, carboplatin or the known cyanide antidote hydroxocobalamin dissolved in dimethylsulfoxide (DMSO) in a five point dose response curve (FIG. 1A-C). Under these conditions, a dose of 100 µM hydroxocobalamin completely blocked cyanide-induced lethality (FIG. 1D). Carboplatin was not a cyanide antidote while cisplatin displayed similar efficacy as hydroxocobalamin. Survival of 100% of zebrafish was observed at 125 µM cisplatin which is approximately equimolar to the cyanide concentration (FIG. 1D).

An ultraviolet-visible (UV-VIS) spectrophotometry experiment was conducted to show that cyanide binds to the positively charged Pt atom. Increasing amounts of potassium cyanide were added to a solution of 1 mM cisplatin in 0.1% DMSO/$H_2O$ and the absorbance was measured across the UV-VIS spectrum. At concentrations ranging from 1-200 mM cyanide a spectral shift was observed at 255 nm (FIG. 1E). At approximately 25 mM cyanide, the reaction between cyanide and cisplatin (1 mM) reached saturation (FIG. 1F). These results indicate that cyanide binds cisplatin and suggests that the mechanism of action of platinum complexes may involve binding of the cyanide anion to the metal core of cisplatin.

ESI-MS was performed to identify the composition of the reaction products created by the addition of cyanide to cisplatin. The spectra contained a major peak with an m/z of 337.9 and minor peaks with m/z's of 272.9 and 350.9 (FIG. 1G). Using MS/MS and isotope distribution comparison, we identified the major peak as platinum bound to 4 cyanide anions and the minor peaks as platinum bound to 3 cyanide anions. See Table 1.

TABLE 1

Identification of the products generated from the reaction between cyanide and cisplatin (DMSO) using isotope distribution comparison of $K^{12}C^{14}N$ versus $K^{13}C^{15}N$

| Species | Peak in $K^{12}C^{14}N$ | Peak in $K^{13}C^{15}N$ | Mass Difference |
|---|---|---|---|
| [Pt(CN)$_4$] | 337.9 | 345.9 | 8 |
| [Pt(CN)$_3$] | 272.9 | 278.9 | 6 |
| [Pt(CN)$_3$DMSO] | 350.9 | 356.9 | 6 |

This finding suggests that platinum complexes may act as antidotes to cyanide poisoning by chelating cyanide anions via the platinum atom.

Example 2—Stability of Cyano-Platinum Complexes In Vivo

Cyano-platinum complexes are considered strong metal cyanide complexes because they do not dissociate easily at physiological pH (Ref. 25). To determine if cyanide dissociates from cyano-platinum complexes in vivo and if the released cyanide induces toxicity, zebrafish were treated with 1-1000 µM potassium cyanide (KCN) or potassium tetracyanoplatinate(II) [$K_2Pt(CN)_4$] for 24 hours. KCN treatment at a dose of 20 µM resulted in 100% lethality. In contrast, zebrafish treated with $K_2Pt(CN)_4$ were alive and active with no gross morphological defects at all doses of $K_2Pt(CN)_4$ tested. These results suggest that the cyano-platinum species produced by administration of a platinum based cyanide antidote are relatively non-toxic.

Example 3—Platinum Based Antidotes

In the case of cisplatin, upon exposure to the intracellular aqueous environment, an associative substitution reaction occurs in which the chloride leaving groups are replaced by water molecules Ref 24). This complex enters the nucleus and a second associative substitution reaction occurs. Purine bases displace the water leaving groups, generating two DNA adducts per cisplatin molecule (Ref. 11). In the case of cyanide exposure, the carbon of the cyanide anion is the nucleophile that forms a bond with the platinum atom and displaces a ligand of the platinum complex.

Figure 2:
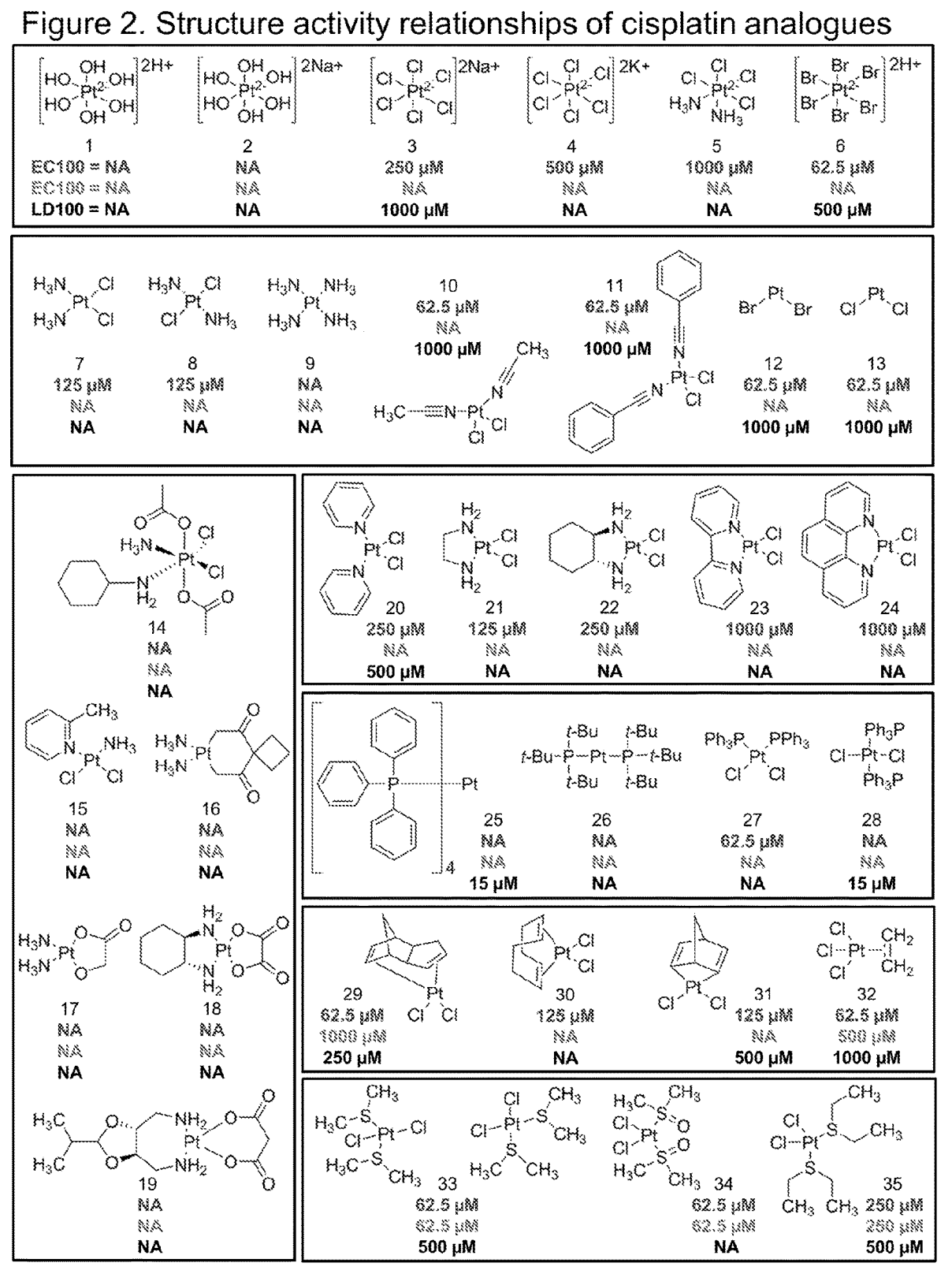

A panel of 35 structurally diverse cisplatin analogs was assembled and doses of 1-1000 µM were tested (10 point dose response curve). The doses that rescued 100% of zebrafish ($EC_{100}$) from a challenge with 100 µM KCN were determined. In a separate assay, the doses that caused 100% lethality ($LD_{100}$) in the absence of KCN were determined. The $EC_{100}$ was determined in both DMSO and PBS solvents (FIG. 2, top and middle value, respectively). The $LD_{100}$ was determined for complexes dissolved in DMSO (FIG. 2, bottom value). NA indicates instances in which the complex did not induce any toxicity or did not rescue cyanide lethality at any of the doses tested. The cisplatin analogs spanned the following classes: platinum (IV) (1-6), square planar (7-13), FDA approved drugs (14-19), pyridine (20-24), triphenylphosphine (25-28), alkene (29-32), and sulfur-containing complexes (33-35).

Platinum (IV) Complexes.

Tetravalent platinum complexes have an octahedral geometry and a coordination number of 6. Complexes with hydroxyl groups (1-2) displayed no toxicity in zebrafish and were not cyanide antidotes at any of the doses tested. Increasing the number of chloride ligands from 2 (7) to 4-6 (3-5) reduced the efficacy of the antidote from 125 µM to 250-1000 µM. The increased efficacy and toxicity of the sodium salt (3) compared to the potassium salt (4) may be due to its greater aqueous solubility. The most effective complex (6) had bromide leaving groups ($EC_{100}$=62.5 µM). Platinum IV complexes with ligands that are good leaving groups were more effective cyanide antidotes than those with poor leaving groups (—Br>—Cl>—OH>—$NH_3$). These results suggest that the ease with which the leaving groups are lost is important to efficacy of platinum based cyanide antidotes.

Square Planar Complexes.

These complexes have a square planar geometry with a coordination number of 4. Both cisplatin (7) and its trans stereoisomer transplatin (8) were equipotent antidotes. In contrast, the cisplatin analog with 4 ammonia ligands (9)

was completely ineffective as an antidote, likely due to the fact that —$NH_3$ is a poor leaving group and typically is considered to be a stable ligand in platinum complexes. The 4 other compounds in this class (10-13) were more potent than cisplatin with minimal toxicity in zebrafish. The two complexes with nitrile ligands (10-11) were effective antidotes at 62 µM. The two least sterically hindered platinum complexes tested in this study had a coordination number of 2, a bent geometry, and either 2 bromide or 2 chloride ligands. Both were effective antidotes at 62 µM (12-13). As a group, these complexes were a potent class of antidotes suggesting that square planar or bent complexes can be effective cyanide chelators.

FDA Approved Drugs and Compounds in Clinical Evaluation.

Many of the compounds in this class (14-19) have a bidentate carboxyl ligand which is a moderate leaving group (16-19). Except for satraplatin (14), they all have a coordination number of 4, and are divalent. The lipophilic Pt (IV) complex satraplatin (14) is an orally available prodrug which to be active must be converted to a Pt (II) complex by loss of the two axial acetate groups. In our assay, it displayed no toxicity however it was not a cyanide antidote. Complex 15 (picoplatin) is a square planar complex that contains a methyl group on the pyridine ring that is perpendicular to the square plane which reduces the substitution kinetics. It also was not a cyanide antidote. Similarly, carboplatin (16), nedaplatin (17), PHM (JM-74) (18) and oxaliplatin (19) were not antidotes when challenged with 100 µM KCN. As a group, this class of complexes displayed no toxicity in zebrafish however none display antidote activity, indicating that compounds with bidentate carboxyl ligands are ineffective as antidotes to cyanide poisoning in zebrafish.

Pyridine Complexes.

Pyridine complexes are divalent cisplatin analogs with two chloride leaving groups and either a pyridine or bidentate pyridine ligand. Whereas complex 15 was developed to contain a methyl group on the pyridine ring that is perpendicular to the square plane thereby reducing the substitution kinetics, complex 20 does not contain a methyl group on either of the pyridine rings. The removal of the methyl group in complex 20 converts the complex into a cyanide antidote although not as effective as cisplatin (250 versus 125 µM). Complexes with bidentate ligands (21-24) displayed decreased efficacy as the size of rings increased suggesting that these rigid ligands may cause steric hindrance that reduces reactivity ($EC_{100}$=1000 µM). Accordingly the most compact complex (21) in this class was the most effective ($EC_{100}$=125 µM). It contains an ethylenediamine group in place of the two ammine groups of cisplatin and displayed no toxicity in zebrafish.

Triphenylphosphine Complexes.

These complexes contain lipophilic triphenylphosphine ligands (25-28). One of the four complexes was an effective antidote at 62.5 µM (27). Its trans stereoisomer (28) was not an antidote potentially due to the bulky triphenylphosphine ligands reducing access to the platinum atom whereas in the cis position the compact nature of the 2 cis chlorides allows access to the platinum atom.

Alkene Complexes.

Alkene complexes are tetrahedral complexes with chloride and alkene ligands (29-32). Complex 32, also known as Zeise's salt, contains a η2-ethylene ligand while the other complexes in the group contain cyclodiene ligands. In this class of compounds the platinum is coordinated to one (32) or two alkenes (29-31). They were equipotent or more effective than cisplatin ($EC_{100}$≤125 µM) and only slightly toxic.

Sulfur-Containing Complexes.

Cisplatin analogs containing two sulfur-based ligands and two chloride ligands (33-35) were tested. The three complexes were effective antidotes at 62.5-250 µM. The change from diethylsulfide ligands in complex 35 to sulfoxide ligands in complex 34 increased efficacy from 250 to 62.5 µM and decreased toxicity. The cis/trans racemic mixture of complex 33 which contains dimethylsulfide ligands compared to complex 35 which contains diethylsulfide ligands was a more potent antidote (62.5 vs 250 µM). It is unclear if the cis or trans stereoisomer was conferring the dominant effect.

Results:

In a panel of 35 platinum complexes, 22 cyanide antidotes with an $EC_{100}$ of 62.5-1000 µM were identified. The two most effective and least toxic antidotes in zebrafish were the triphenylphoshine complex 27 and the sulfur-containing complex 34 ($EC_{100}$=62.5 µM and no observed toxicity in zebrafish). However, complex 27 is poorly soluble in water (0.079 g/L, log P=8.2) whereas complex 34 is aqueous soluble (84 g/L; log P=−1.35). This is a ~33 fold improvement in solubility over cisplatin (2.5 g/L with a log P=−2.19). Additionally, the reported dose of complex 34 that causes acute toxicity in mice is ~20 fold higher than cisplatin ($LD_{50}$=133 versus 6.6 mg/kg IP) (Ref. 6).

PBS Solvated Complexes:

Surprisingly, when cisplatin analogs were dissolved in PBS, the majority were not cyanide antidotes at any dose tested (FIG. 2). However, 2 of the 4 alkene complexes (29 and 32) were antidotes, albeit requiring doses 16 and 8 fold higher, respectively, than when solvated in DMSO. All three sulfur-containing complexes (33-35) were equipotent antidotes when dissolved in DMSO and PBS. These findings motivated us to explore the effects of solvation on the efficacy of cisplatin analogs as cyanide antidotes.

Example 4—Cis-Diamminechloro(Dimethylsulfoxide)Platinum(II) (Complex 36) Binds Cyanide Faster than Cis-Diamminedichloroplatinum(II) (Cisplatin)

Cisplatin's mechanism of action requires aquation, the replacement of the chloride ligands with water molecules. This generates the active form of cisplatin (37) which is more reactive than the chloride complex (7). Due to the high concentration of chloride ions in the blood (~100 mM) versus inside the cell (~4 mM), aquation is favored once cisplatin enters the cell. When cisplatin is dissolved in dimethylsulfoxide (DMSO), the sulfur in DMSO undergoes nucleophilic attack of platinum. This results in the substitution of a chloride ligand with a DMSO ligand, changing its structure and creating a new chemical species (36). These results show that DMSO leaving group influences the kinetics of the reaction with cyanide.

UV-VIS experiments were conducted to determine if dissolving cisplatin in PBS versus DMSO affected cyanide binding. Cisplatin was dissolved in water generating the aquated form of cisplatin (37), in PBS preventing the chloride ligands from being displaced by water molecules (7), or in DMSO creating the DMSO-adduct species (36) (FIG. 3A, C, E). In complex 37, cyanide would be predicted to displace a water ligand first (FIG. 3A). In complex 7, the cyanide anion would be predicted to displace a chloride ligand first (FIG. 3C). In complex 36, based on previous associative substitution studies with platinum complexes, cyanide would be predicted to displace the ammine ligand (Ref. 3) (FIG. 3E). To determine the binding affinity of cyanide for these three complexes, increasing concentrations of cyanide were added while the absorbance across the UV-VIS spectrum was measured (FIG. 3B, D, F). Both cisplatin (7) and the aquated form of cisplatin (37) did not induce a significant spectral shift when cyanide was added (FIG. 3B, 3D). In contrast, complex 36 induced a significant spectral shift in the presence of increasing concentrations of cyanide (FIG. 3F). Performing this experiment in a polar, aprotic environment did not affect the binding of cyanide to complex 7. These findings suggest that during nucleophilic attack, the cyanide anion cannot easily displace the chloride or water ligands in platinum; however, when a DMSO ligand is conjugated to the platinum complex associative substitution is highly favorable.

Next, a time-course experiment was performed to evaluate the reaction rate of cyanide with these complexes. To 1 mM of complex, 5 mM of cyanide was added and the absorbance was measured every 1 minute for 5 minutes followed by every 5 minutes for 30 minutes (FIG. 3G). Cisplatin (7) dissolved in PBS and assayed in PBS had a reaction rate of 0.021 AU/min. The aquated form of cisplatin (cisplatin dissolved in water and assayed in water, 37) had a reaction rate of 0.013 AU/min. Complex 36 (cisplatin dissolved in DMSO and assayed in water), had a reaction rate of 0.367 AU/min. To create a polar aprotic environment DMF was used as the solvent and assay buffer. Cisplatin dissolved in and assayed in DMF had a reaction rate of 0.019 AU/min. These results demonstrate that the reaction between cyanide and complex 36 occurred at a rate 17 fold faster than cisplatin (7) and 28 fold faster than the aquated form of cisplatin (37).

Example 5—Identification of Complex 36 as a Cyanide Antidote In Vivo

Zebrafish treated with cisplatin dissolved in PBS (cisplatin) displayed no activity as a cyanide antidote while cisplatin dissolved in DMSO (complex 36) was an effective antidote (FIG. 3H). Theoretically DMSO could undergo nucleophilic attack of the platinum atom, generating multiple reaction products. To decipher the exact chemical species created when we dissolved cisplatin in DMSO, ESI-MS was used. The most abundant ion signal detected was at m/z=343 corresponding to the molecular weight of [Pt(NH$_3$)$_2$(Cl)(DMSO)] (FIG. 3I). In this complex one chloride ligand was displaced by a DMSO ligand generating cis-diamminechloro(dimethylsulfoxide)platinum(II) (36). We observed near complete conversion of cisplatin to complex 36 within a few hours, consistent with the literature (Ref 12). Other minor species were detected consistent with published studies (Table 2).

TABLE 2

Peaks observed for ESI+ mass spectra of cisplatin dissolved in DMSO

| Species | Formula | Observed Mass | Calculated Mass |
| --- | --- | --- | --- |
| [Pt(NH3)2(Cl)(DMSO)]+ | C2H12ClN2OPtS | 342.9996 | 343.0085 |
| [Pt(NH3)(Cl)(DMSO)2]+ | C4H15ClNO2PtS2 | 403.9868 | 403.9959 |
| μNH2—[Pt(NH3)(Cl)(DMS0)]2+ | C4H20Cl2N3O2Pt2S2 | 665.9661 | 665.9670 |

Collectively these results demonstrate that the cisplatin analog, cis-diamminechloro(dimethyl sulfoxide)platinum (II), is a cyanide antidote. Complexes of compounds lacking a sulfur ligand (e.g., Pt chemotherapeutic agents) when dissolved in DMSO are good cyanide antidotes, whereas those same complexes dissolved in PBS may not always be cyanide antidotes suggesting that sulfur based ligands are important to platinum based cyanide antidotes Example 6—Toxicity of Complex 36 In Vitro Results of this experiments are shown in FIGS. 4 and 7. The toxic side effects of platinum based drugs are thought to be due to their mechanism of action, DNA damage leading to cell death. DMSO is known to inactivate chemotherapeutic drugs (cisplatin, carboplatin and oxaliplatin) by inserting into the complex, disrupting its ability to interact with DNA and hence induce cell death (Ref 12). To test the cytotoxicity of the compounds under study, cisplatin responsive non-small cell lung cancer cells (H1975) were used. Cells were treated with 0-300 μM of a platinum complex for 72 hours and cell viability was assessed by measuring ATP levels. Cells treated with 50 μM cisplatin appeared rounded, shrunken and fragmented, while those treated with complexes 36 or 34 displayed similar morphology to control cells (FIG. 4A). At 72 hours, dose dependent cell killing was observed in cisplatin treated cells, however not in cells treated with complex 34 or 36 (FIG. 4B). The IC$_{50}$ for cisplatin was 62 μM. In an expanded dose response curve, the IC$_{50}$ of complexes 34 and 36 were 702 and 689 μM, a ~10 fold decrease in cytotoxicity.

Activation of p38 MAPK in response to cisplatin induced DNA damage is a requisite step in the mechanism of action of cisplatin (Ref. 14). We measured the phosphorylation state of the kinase p38 MAPK in lysates from cells treated with 50 μM of the indicated complexes for 24 hours. As expected, cisplatin activated p38 by inducing phosphorylation (FIG. 4C). However, complexes 34 and 36 did not increase activated p38 levels, indicating that these complexes are not initiating the stress-associated signaling pathway that is triggered by cisplatin. These findings are consistent with previous in vitro and in vivo studies demonstrating the detoxifying effect of DMSO formulations of cisplatin (Ref. 17).

Although the DMSO-bound form of cisplatin undermines the drug's utility as a chemotherapeutic drug, the decreased toxicity is a beneficial aspect for its use as a cyanide antidote. These findings indicate that the DMSO adducts of structurally distinct platinum chemotherapeutic agents exhibit reduced cytotoxicity while maintaining or improving their efficacy as cyanide antidotes.

Example 7—Test Compounds Protected Mice Exposed to a Lethal Dose of Cyanide

In the mouse model of cyanide poisoning, a mouse is placed in a gas tight chamber and exposed to cyanide gas for 15 minutes. Subsequently, the mouse is injected intraperitoneally with vehicle or platinum complex and then re-exposed to cyanide gas for 25 minutes. Thus, total exposure time to cyanide gas is 40 minutes. All surviving animals are observed for several hours and then euthanized. In this model mice that receive saline consistently died within a 5 minute window 30-35 minutes after the onset of cyanide exposure (n=6).

Pt(II) and Pt(IV) compounds (36, 34 and 3) were chosen based on efficacy/toxicity in zebrafish, toxicity in human cells, binding kinetics, and solubility. Several other complexes had favorable efficacy and toxicity profiles however due to low solubility they will require future formulation studies prior to mammalian testing. Of the mice receiving complex 36 (20 µmol), 83% survived the full exposure period (n=6) while of those receiving 10 µmol 33% survived (n=6). Of the mice receiving 20 µmol complex 34, 100% survived while of those receiving 10 µmol, 33% survived (n=6). For complex 3, 100% of mice receiving 5 µmol and 50% of mice receiving 2.5 µmol survived (n=6). The four-fold increased potency of complex 3 compared to complex 36 may be because complex 3 binds up to 5 cyanide anions while complex 36 binds 3-4 cyanide anions (FIG. 8). Results of these experiments are shown in FIGS. 5 and 8. Collectively, these data demonstrate that the effect of cisplatin analogs as countermeasures to cyanide poisoning is conserved in mammals.

Example 8—Formulation in DMSO Improves Efficacy of Platinum Based Cyanide Antidotes Complex 3 was tested with or without DMSO. Treatment with 2.5 µmol of complex 3 formulated with DMSO resulted in 50% survival (n=6). To achieve 66% survival in mice treated with complex 3 formulated without DMSO, a dose of 10 µmol was required (n=6). These results indicate that DMSO formulation improves the efficacy of complex 3 by ~4-fold and suggests that the improvement in antidote activity is a result of the chemical reaction between DMSO and platinum complexes.

Example 9—Test Compounds Reversed Cyanide-Induced Effects on Oxidative Metabolism in Rabbits Rabbits (n=5) were infused intravenously (IV) with a sub-lethal dose of sodium cyanide (10 mg) while tissue oxygenation in the central nervous system (CNS) was monitored in real time using continuous wave near infrared spectroscopy (CWNIRS). During the 60 minute cyanide infusion, CWNIRS of the CNS detected an increase in the concentration of oxyhemoglobin and decrease in deoxyhemoglobin (FIG. 6A). This occurs as cyanide prevents oxygen offloading from hemoglobin in erythrocytes thus leading to an increasing fraction of hemoglobin in the oxygenated state. However when the cyanide infusion stops, both of these curves gradually reverse, indicating oxygen offloading from hemoglobin and an increase in circulating hemoglobin in the deoxygenated state (blue). Thus, the pathophysiological changes associated with sub-lethal cyanide exposure are reversed 30 minutes following the cessation of cyanide infusion.

To determine if cisplatin analogs alter the kinetics of oxygen offloading from hemoglobin and ameliorate cyanide toxicity in the CNS, rabbits were treated with 15 mg/kg of 36 or 7.5 mg/kg of 3 IV after the cyanide infusion (n=5). There is no rabbit toxicity data on 34, 36 or the complex 3 DMSO adduct species in the literature, but the doses of 3 that were used are well above the LDLo in rabbits (7.5 mg/kg vs 180 mg/kg) (TOXNET). As expected, during cyanide infusion, an increase in the concentration of oxyhemoglobin and decrease in deoxyhemoglobin was detected, indicating cyanide toxicity. However, immediately following the administration of 36 or 3 (Inj), the oxy- and deoxyhemoglobin concentrations rapidly returned to baseline levels (FIG. 6B, E). Restoration to baseline occurs in less than 10 minutes compared to vehicle controls in which restoration to near baseline occurs in 30 minutes (intersection of oxy- and deoxy-hemoglobin curves). Further, the time constant (Tau) which represents the decay of the oxy-hemoglobin was significantly different compared to controls (257±143 min; p<0.01) for both complex 3 and complex 36 (6.61±4.41 and 12.15±4.42 min, respectively). Collectively, these changes indicate a reversal of the pathophysiological events induced by cyanide.

Example 10—Metabolism of Platinum-Based Antidotes

Experimental results indicate that the elimination pathway for cyano-platinum complexes in mammals occurs via the kidneys as both thiocyanate and cisplatin are excreted in the urine. Urine was collected 90 minutes post antidote injection and cyano-platinum complexes were measured by mass spectrometry. 1.3±0.7 µg/mL of $Pt(CN)_3$ and 0.6±0.3 µg/mL of $Pt(CN)_4$ were detected in the urine of rabbits (n=3) treated with complex 36. In rabbits (n=3) treated with complex 3, 30.5±17.6 µg/mL of $Pt(CN)_3$ and 12.9±7.5 µg/mL of $Pt(CN)_4$ were detected in the urine 90 minutes post injection. These data demonstrate that cyano-platinum species produced by the administration of platinum based antidotes are excreted into the urine.

Example 11—Platinum Compounds Administered IV Corrected Cytochrome C Oxidase Redox State in Rabbits Exposed to Cyanide Diffuse optical spectroscopy (DOS) was used to monitor cytochrome c oxidase redox state in the muscle of rabbits. During the 60 minute cyanide infusion, the cytochrome c oxidase redox ratio decreased due to the binding of cyanide anion to iron in cytochrome c oxidase and did not return to baseline levels after cessation of the cyanide infusion (FIG. 6B). However, when 13 mg/kg of compound 36 or 7.5 mg/kg of compound 3 (HCP) (n=5) was injected IV, cytochrome c oxidase redox ratio returned to baseline in 10-20 minutes (FIGS. 6D, 6F). These findings indicate that tested compounds restore muscle cytochrome c oxidase redox state to baseline, indicating that test compounds are effective antidotes in mammals.

Example 12—Intramuscular Injection of HCP Rescues Rabbits from Exposure to a Lethal Dose of Cyanide IV administration of HCP to rabbits exposed to a sublethal dose of cyanide rapidly reverses cyanide-induced inhibition of oxygen offloading from hemoglobin and accelerates recovery from cyanide toxicity (see Example 11). In this example, an established rabbit protocol was used, in which exposure to cyanide results in death within 40 minutes of cyanide infusion unless an antidote is administered. Lethal cyanide dose was achieved by intravenous administration of 20 mg sodium cyanide (0.33 mg/min) until blood pressure dropped below 60 mmHg (~20-40 minutes), at which time antidote (30 mg/kg HCP IM) or saline was administrated (FIG. 9A). Cyanide infusion continued for another 30 minutes. During the experimental sequence, serial blood samples were collected (FIG. 9A). This model resulted in lethality for 9 of 11 (81%) saline-treated rabbits, whereas only 2 of 9 (22%) HCP-treated rabbits died (p=0.02; FIG. 9B). Further these 7 rabbits survived the full experimental follow-up period of 220 minutes demonstrating that HCP is an effective antidote to a lethal dose of cyanide and, importantly establishing that HCP is effective via intramuscular administration.

In this model, cellular cytochrome c oxidase redox state and oxy-/deoxy-hemoglobin are monitored using diffuse optical spectroscopy (DOS) from a probe placed on the shaved surface of the right inner thigh muscle (FIG. 9C). Typically, during cyanide poisoning, cellular cytochrome c oxidase redox state steadily decreases over the 40 minute infusion (due to the binding of cyanide anions to iron in cytochrome c oxidase (−0.05±0.02 to −1.43±0.11 μM, p=1E-10; FIG. 9D). By contrast, in animals treated with HCP at t=40, cytochrome c oxidase redox state plateaus after antidote injection demonstrating HCP halts the deleterious effects of cyanide on cytochrome c oxidase (FIGS. 9C and 9E). Concordant protective effects of HCP are observed on the parameters of oxygenated and deoxygenated hemoglobin (FIG. 9C). These results indicate that HCP also restores parameters of cellular physiology.

Example 13—HCP Relieves the TCA Cycle Blockage Induced by Cyanide

Orthogonal approach was used to further evaluate the mechanism of antidote efficacy, measuring TCA cycle metabolites by mass spectrometry. As expected, cyanide infusion resulted in significant changes in TCA cycle metabolites due to inhibition of cellular respiration. This led to increased concentrations of TCA cycle metabolites as their consumption slowed down: α-ketoglutaric acid (+336±27%; p=8E-05), succinic acid (+1907±259%; p=0.0009), fumaric acid (+1241±270%; p=0.0006), and malic acid (+329±64%; p=5E-05) (FIGS. 10A-10D). By contrast, treatment with HCP returned α-ketoglutaric acid levels to near baseline (+75±17%); excursion of succinic acid (+429±82%), fumaric acid (+310±63%) and malic acid (+218±31%) were also significantly abrogated. Additionally, glycolytic metabolites are increased including pyruvic acid (+794±106%; p=0.001) and lactic acid (+245±64%; p=0.001). These metabolites plateaued after HCP administration. Together these findings indicate that HCP activates TCA cycle metabolism, allowing the metabolites in this pathway to be consumed.

Example 14—HCP is Absorbed Rapidly and Scavenges Multiple Cyanide Ions

Pharmacokinetic analyses were performed to monitor the associative substitution reaction of cyanide and HCP in vivo. Baseline and serial blood sampling was performed over 220 minutes and analyzed using mass spectrometry. A representative mass spectrograph is displayed in FIG. 11A, demonstrating the profile of HCP-cyanide species identified in rabbits.

Shortly after IM injection of HCP at t=40, HCP is detected in blood (t=42.5). The observed HCP sera $C_{max}$ was 148±52 nM HCP and the observed $t_{max}$ was 7.5 minutes (FIG. 11B). As HCP levels diminished (half-life=19 minutes), we observed increased levels of several PtCN species including tricyanoplatinate, tetracyanoplatinate and pentacyanoplatinate (FIG. 11B, n=7). Sera $C_{max}$ was 1.52±0.02, 2.67±0.85 and 7.65±0.02 μM for $PtCN_3$, $PtCN_4$ and $PtCN_5$, respectively. Sera $t_{max}$ was 7.5 minutes for all three HCP-CN species. Notably, HCP-CN species were detected 2.5 minutes post antidote injection, indicative of the rapid uptake of HCP and sequestration of cyanide by HCP. Further, HCP binds 3-5 cyanide anions in vivo. The predominant species is $PtCN_5$ displaying 5-fold and 3-fold greater levels than $PtCN_3$ and $PtCN_4$, respectively. The pharmacokinetic profiles of HCP and HCP-cyanide species demonstrate the early bioavailability of HCP and its rapid scavenging of cyanide.

Example 15—Surrogate Biomarkers of Adverse Drug Reactions do not Change During Acute HCP Exposure in Rabbits The metabolite platform used monitors surrogate markers of adverse drug reactions including creatinine (kidney function), glucose (glycemic homeostasis), histamine (allergic reaction), lactic acid (acidosis), and bile acids (liver function). Rabbits were anesthetized, ventilated and lines were placed, using the exact procedure used for cyanide infusion experiments. However, in these experiments rabbits were infused with saline for 60 minutes (n=3). Following saline administration, HCP (30 mg/kg) was given intramuscularly, and plasma metabolite measurements were measured serially for 220 minutes (FIGS. 12A-12E). No significant changes were observed between baseline and t=220 minutes across the range of metabolite biomarkers of drug toxicity excluding the major mechanisms of an acute adverse drug reaction during this timeframe. Given these findings, we next formally assessed safety in mice.

Example 16—Toxicity Studies in Mice Treated with HCP Reveal Normal Blood Chemistry and No Major Organ Toxicity Mice were treated with a single dose of vehicle or HCP (200 mg/kg, IM) and monitored for 4 days. Subsequently, blood was collected for Comprehensive Metabolite and Complete Blood Count panels, and all organs were harvested for histological analysis (see Tables 3 and 4, n=11 HCP, n=4 controls).

TABLE 3

Comprehensive Metabolic Panel Results in Mice 4 days after Treatment with 200 mg/kg IM HCP or Vehicle

| Analyte | Ref. Range | Control | HCP | P Value |
|---|---|---|---|---|
| GLU | 172-258 mg/dL | 196.00 ± 15.04 | 186.00 ± 10.5 | 0.777 |
| BUN | 16-21 mg/dL | 16.80 ± 1.25 | 13.70 ± 0.45 | 0.009 |
| CREA | 0.10 mg/dL | 0.20 ± 0.00 | 0.20 ± 0.01 | 0.249 |
| PHOS | 8.6-10.2 mg/dL | 8.20 ± 0.55 | 9.70 ± 0.39 | 0.124 |
| CA | 9.5-10.3 mg/dL | 10.50 ± 0.06 | 10.50 ± 0.11 | 0.866 |
| NA | 154.4-158.8 mmol/L | 145.70 ± 0.33 | 146.30 ± 0.57 | 0.740 |
| K | 10.0-7.8 mmol/L | 4.60 ± 0.28 | 4.80 ± 0.19 | 0.625 |
| CL | 96.1-134.1 mmol/L | 107.30 ± 1.33 | 108.10 ± 0.78 | 0.755 |
| TP | 5.1-5.7 g/dL | 4.90 ± 0.03 | 4.90 ± 0.07 | 0.900 |
| ALB | 2.2-2.4 g/dL | 2.50 ± 0.03 | 2.50 ± 0.04 | 0.565 |
| GLOB | 2.9-3.3 g/dL | 2.40 ± 0.00 | 2.50 ± 0.03 | 0.349 |
| A/G | 0.8 (ratio) | 1.00 | 1.00 | 0.104 |
| ALT | 37.6-85.8 U/L | 52.00 ± 9.17 | 40.80 ± 1.05 | 0.073 |
| ALP | 58.7-104.7 U/L | 119.70 ± 7.31 | 92.30 ± 7.78 | 0.099 |
| TBIL | 0.1-0.3 mg/dL | 0.50 ± 0.09 | 0.70 ± 0.08 | 0.416 |
| CHOL | 114.4-163.4 mg/dL | 106.70 ± 18.11 | 101.70 ± 4.16 | 0.715 |
| AMY | 1691-3615 U/L | 2384.50 ± 111.45 | 1948.80 ± 61.86 | 0.056 |

TABLE 4

Complete Blood Count Panel Results in Mice 4 days after Treatment with 200 mg/kg IM HCP or Vehicle

| CBC | Ref. Range | Control | HCP | P Value |
|---|---|---|---|---|
| TP (R) | 5.1-5.7 g/dL | 18.10 ± 13.2 | 4.90 ± 0.09 | 0.221 |
| RBC | 8.4-11.0 M/uL | 7.61 ± 0.13 | 7.70 ± 0.20 | 0.839 |
| HCT | 47.2-55.7% | 44.40 ± 0.90 | 43.90 ± 1.07 | 0.713 |

TABLE 4-continued

Complete Blood Count Panel Results in Mice 4 days
after Treatment with 200 mg/kg IM HCP or Vehicle

| CBC | Ref. Range | Control | HCP | P Value |
|---|---|---|---|---|
| HGB | 13.8-16.6 g/dl | 13.10 ± 0.20 | 12.50 ± 0.31 | 0.250 |
| MCV | 54.0-57.8 fL | 58.40 ± 1.32 | 57.20 ± 0.57 | 0.345 |
| MCHC | 29.4-30.2 g/dL | 29.50 ± 0.32 | 28.60 ± 0.40 | 0.193 |
| RDW | % | 13.10 ± 0.77 | 14.60 ± 0.25 | 0.064 |
| WBC | 4.8-9.8 K/uL | 4.50 ± 0.35 | 3.70 ± 0.33 | 0.174 |
| SEG | K/uL | 0.80 ± 0.15 | 0.80 ± 0.24 | 0.881 |
| LYMPH | 77-8-88.4 K/uL | 3.10 ± 0.58 | 2.60 ± 0.12 | 0.359 |
| MONO | 0.9-4.9 K/uL | 0.27 ± 0.09 | 0.20 ± 0.08 | 0.655 |
| EOS | 1.2-2.6 K/uL | 0.40 ± 0.20 | 0.10 ± 0.02 | 0.066 |
| RETIC | 387.9-400.8 K/uL | 373.1 ± 39.68 | 825.3 ± 66.14 | 0.003 |

No acute kidney dysfunction was detected in HCP versus control treated mice as demonstrated by the lack of statistically significant differences in creatinine (0.20±0.01 vs 0.20±0.00 mg/dL, respectively) and phosphate levels (9.70±0.39 vs 8.20±0.55 mg/dL). Further electrolytes were normal in HCP treated mice versus controls (calcium 10.50±0.11 vs 10.50±0.06 mg/dL, sodium 146.30±0.57 vs 145.70±0.33 mmol/L, potassium 4.80±0.19 vs 4.60±0.28 mmol/L and chloride 108.10±0.78 vs 107.30±1.33 mmol/L). Additionally, there were no significant differences in alanine aminotransferase (40.80±1.05 vs 52.00±9.17 IU/L), alkaline phosphatase (92.30±7.78 vs 119.70±7.31 IU/L), and total bilirubin (0.70±0.08 vs 0.50±0.09 mg/dL) in HCP compared to control treated mice, respectively, excluding early hepatotoxicity. Amylase, a marker of pancreatic dysfunction, was not significantly different between controls (2384.50±111.45 IU/L) and HCP (1948.80±61.86 IU/L) treated animals. Blood urea nitrogen, BUN, (13.70±0.45 vs 16.80±1.25 mg/dL; p=0.009) was statistically different between groups, but both groups were lower than the normal reference range for CD-1 mice indicative of an underlying factor affecting BUN in these particular mice (19-29 mg/dL). Cumulatively, these clinical findings demonstrate that 200 mg/kg IM HCP is well tolerated by mice.

A Complete Blood Count panel revealed no significant differences in erythrocytes, leukocytes, eosinophils, monocytes or lymphocytes (Table 4). The only significant difference was increased reticulocytes (825.3±66.14 vs 373.1±39.68 K/uL; p=0.003). For reference, the normal reticulocyte values in CD-1 mice range between 200-500 K/uL, which in general is higher than most other species due to their relatively short life spans. Acute muscle necrosis was identified at the injection site (hind limb) on gross and histologic evaluation. Neutrophils and erythrocytes were primarily associated with the necrotic muscle, and inflammation occasionally extended into the deep subcutis. Formulation studies are currently underway to overcome HCP-induced injection site injury. Pathologic lesions were not identified in lung, heart, liver, spleen, kidney, and brain. In summary, these preliminary toxicity studies demonstrate that HCP does not induce organ toxicity and further the most concerning toxicity anticipated for platinum analogs, i.e. renal damage, is not observed after HCP administration.

Further, HCP exhibits an □33-fold improvement in solubility over cisplatin and an ~20-fold lower reported toxicity in mice than cisplatin ($LD_{50}$=133 versus 6.6 mg/kg). Preliminary toxicity studies demonstrate that the most concerning toxicity anticipated for platinum analogs, i.e. renal damage, was not observed after HCP administration. The only lesion observed was muscle necrosis at the injection site, which likely may be mitigated by compound formulation.

Example 17—Replication of Survival, Pharmacokinetic and Metabolite Findings in a Pilot Study in a Swine Model of Cyanide Poisoning A study was conducted to test the efficacy of HCP in a swine model. The model is designed to mimic an out of hospital, acute cyanide exposure scenario, such as during a fire or a terrorist attack. Animals are not mechanically ventilated, allowing them to become apneic following intravenous administration of potassium cyanide. Pigs are held at apnea for 5 minutes, and subsequently administered vehicle control or antidote. Invasive blood pressure is monitored continuously and blood sampling occurs serially throughout both the exposure and recovery phases of the model. In vehicle treated animals, death occurs in 100% of cases within 60 minutes following cyanide exposure. Whereas, pigs treated with 20 mg/kg HCP IM (n=3) all survived to the endpoint of the study, 110 minutes after commencing cyanide infusion (FIGS. 13A-13B). These preliminary findings suggest HCP also confers protection in a swine model of severe, lethal cyanide poisoning.

Shortly after intramuscular administration of antidote, we detected 0.99±0.18 μM of HCP in the circulation at 5 minutes post antidote injection (FIG. 13C), similar to the rapid absorption in the rabbit model (2.5 minutes post injection, FIG. 11B). The concentration of HCP steadily rose over the next 30 minutes, reaching a $C_{max}$ of 4.79±0.95 μM at 35 minutes post antidote injection. Subsequently, HCP concentration plateaued. By t=110 (95 minutes post antidote injection), the levels declined to 1.91±1.50 μM, exhibiting a half-life of 91 minutes in this model (FIG. 13C). Similar to the observations in the rabbit model, HCP formed HCP-$CN_3$, -$CN_4$ and -$CN_5$ species in swine model. As in the rabbit model, $PtCN_5$ is the predominant species. In this model, $PtCN_5$ displayed a $C_{max}$ of 2.60±0.47 μM and a $t_{max}$ of 12.5 minutes (FIG. 5C). In contrast to the rabbit model, HCP was cleared slower and HCP-CN species were cleared faster.

At t=110, no Pt-CN species were detectable in the blood. $PtCN_5$ displayed a half-life of 17 minutes. Therefore, excretion of HCP-CN species in the urine was evaluated at baseline and at various time-points post antidote delivery (FIG. 13D). We detected increasing concentrations of all three PtCN species in the urine following antidote injection. The highest concentration detected in the urine was at the last time-point measured ($PtCN_3$=8.5±4.3, $PtCN_4$=6.9±3.4, and $PtCN_5$=4.8±2.4 μM, respectively, FIG. 13D). These findings demonstrate that, in a large mammalian model, HCP is rapidly absorbed after IM administration, quickly reacts with cyanide, binding up to 5 cyanide anions, and HCP-CN species are excreted into the urine.

Metabolite profiling revealed many similarities in HCP-induced effects in the swine compared to the rabbit, though some differences were observed (FIGS. 13E-13J). Concordant with the rabbit model, the most pronounced changes were in succinic acid (+1277±426%; p=0.05, FIG. 13H); significant increases in α-ketoglutaric acid (+245±10%, p=0.03), fumaric acid (+325±23%, p=0.04) and malic acid (+462±54%, p=0.001) were also observed. In rabbits, TCA cycle metabolites accumulate during the cyanide infusion period and slowly return to toward baseline levels (FIG. 10). Even more pronounced relief of TCA cycle block was observed in the pig model following HCP injection: succinic acid (+137±213%, FIG. 13H), fumaric acid (+108±54%, FIG. 13I) and malic acid (+162±69%, FIG. 13J). Malic acid peaked at +245±66% and remained elevated (+212±62%), in contrast to the rabbit model in which this metabolite trended towards baseline (FIG. 13F).

Interestingly, injection of HCP had immediate effects on pyruvate metabolism in the swine model that were not observed in the rabbit model (FIG. 10A). In the swine model, infusion of cyanide resulted in peak pyruvate levels at t=20 minutes (+550±98%; p=0.001, FIG. 13E). At this point antidote was injected and 2.5 minutes post antidote administration, we observed peak levels of $PtCN_5$. Over the same period of time there was a significant drop in pyruvate levels (+550±98% to +362±68%; p=0.05). During the remainder of the experimental protocol pyruvate levels remained steady. Lactic acid levels increased to +362±48%, plateaued and began to decline at t=90 (FIG. 13F), whereas in the rabbit model lactic acid plateaued and remained elevated (FIG. 10B). Compared to the rabbit model, these data demonstrate concordant effects on TCA cycle metabolism, in addition to unique metabolic effects in the pig model. Together the findings in the swine study demonstrate that HCP was rapidly absorbed by IM administration, activated TCA cycle metabolism, and improved survival.

REFERENCES

1. Alcorta, R. (2004). Smoke inhalation & acute cyanide poisoning. Hydrogen cyanide poisoning proves increasingly common in smoke-inhalation victims. JEMS 29, suppl 6-15; quiz suppl 16-17.
2. Anderson, M. E., Naganuma, A., and Meister, A. (1990). Protection against cisplatin toxicity by administration of glutathione ester. FASEB J 4, 3251-3255.
3. Banerjea, D., Basolo, F., and Pearson, R. G. (1957). Mechanism of Substitution Reactions of Complex Ions. XII. Reactions of Some Platinum(II) Complexes with Various Reactants. Journal of the American Chemical Society 79, 4055-4062.
4. Barillo, D. J., Goode, R., and Esch, V. (1994). Cyanide poisoning in victims of fire: analysis of 364 cases and review of the literature. J Burn Care Rehabil 15, 46-57.
5. Basolo, F., and Pearson, R. G. (2007). The Trans Effect in Metal Complexes. In Progress in Inorganic Chemistry (John Wiley & Sons, Inc.), pp. 381-453.
6. Braddock, P. D., Connors, T. A., Jones, M., Khokhar, A. R., Melzack, D. H., and Tobe, M. L. (1975). Structure and activity relationships of platinum complexes with antitumour activity. Chem Biol Interact 11, 145-161.
7. Brenner, M., Kim, J. G., Mahon, S. B., Lee, J., Kreuter, K. A., Blackledge, W., Mukai, D., Patterson, S., Mohammad, O., Sharma, V. S., et al. (2010). Intramuscular cobinamide sulfite in a rabbit model of sublethal cyanide toxicity. Ann Emerg Med 55, 352-363.
8. Broughton, E. (2005). The Bhopal disaster and its aftermath: a review. Environ Health 4, 6.
9. Chan, A., Jiang, J., Fridman, A., Guo, L. T., Shelton, G. D., Liu, M. T., Green, C., Haushalter, K. J., Patel, H. H., Lee, J., et al. (2015). Nitrocobinamide, a new cyanide antidote that can be administered by intramuscular injection. J Med Chem 58, 1750-1759.
10. Elschenbroich, C. (2006). Organometallics (Weinheim, Wiley-VCH).
11. Fichtinger-Schepman, A. M., van der Veer, J. L., den Hartog, J. H., Lohman, P. H., and Reedijk, J. (1985). Adducts of the antitumor drug cis-diamminedichloroplatinum(II) with DNA: formation, identification, and quantitation. Biochemistry 24, 707-713.
12. Fischer, S. J., Benson, L. M., Fauq, A., Naylor, S., and Windebank, A. J. (2008). Cisplatin and dimethyl sulfoxide react to form an adducted compound with reduced cytotoxicity and neurotoxicity. Neurotoxicology 29, 444-452.
13. Frantz, M. C., and Wipf, P. (2010). Mitochondria as a target in treatment. Environ Mol Mutagen 51, 462-475.
14. Galan-Moya, E. M., Hernandez-Losa, J., Aceves Luquero, C. I., de la Cruz-Morcillo, M. A., Ramirez-Castillejo, C., Callejas-Valera, J. L., Arriaga, A., Aranburo, A. F., Ramon y Cajal, S., Silvio Gutkind, J., et al. (2008). c-Abl activates p38 MAPK independently of its tyrosine kinase activity: Implications in cisplatin-based therapy. Int J Cancer 122, 289-297.
15. Gopal, K. V., Wu, C., Shrestha, B., Campbell, K. C., Moore, E. J., and Gross, G. W. (2012). d-Methionine protects against cisplatin-induced neurotoxicity in cortical networks. Neurotoxicol Teratol 34, 495-504.
16. Hall, A. H., Saiers, J., and Baud, F. (2009). Which cyanide antidote? Crit Rev Toxicol 39, 541-552.
17. Hall, M. D., Telma, K. A., Chang, K. E., Lee, T. D., Madigan, J. P., Lloyd, J. R., Goldlust, I. S., Hoeschele, J. D., and Gottesman, M. M. (2014). Say no to DMSO: dimethylsulfoxide inactivates cisplatin, carboplatin, and other platinum complexes. Cancer Res 74, 3913-3922.
18. Hao, J., Ho, J. N., Lewis, J. A., Karim, K. A., Daniels, R. N., Gentry, P. R., Hopkins, C. R., Lindsley, C. W., and Hong, C. C. (2010). In vivo structure-activity relationship study of dorsomorphin analogues identifies selective VEGF and BMP inhibitors. ACS Chem Biol 5, 245-253.
19. Harrap, K. R., Jones, M., Wilkinson, C. R., Clink, H. M., Sparrow, S., Mitchley, B. C. V., Clarke, S., and Veasey, A. (1980). Antitumour, toxic and biochemical properties of cis-platin and eight other platinum complexes. In cis-Platin: Current status and new developments, A. W. Prestayko, S. T. Crooke, and S. K. Carter, eds. (New York, Academic Press), pp. 193-212.
20. Ivanov, A. I., Christodoulou, J., Parkinson, J. A., Barnham, K. J., Tucker, A., Woodrow, J., and Sadler, P. J. (1998). Cisplatin binding sites on human albumin. J Biol Chem 273, 14721-14730.
21. Jamieson, E. R., and Lippard, S. J. (1999). Structure, Recognition, and Processing of Cisplatin-DNA Adducts. Chem Rev 99, 2467-2498.
22. Kellin, D. (1929). Cytochrome and respiratory enzymes. Proceedings of the Royal Society B: Biological Sciences 104, 206-251.
23. Nath, A. K., Roberts, L. D., Liu, Y., Mahon, S. B., Kim, S., Ryu, J. H., Werdich, A., Januzzi, J. L., Boss, G. R., Rockwood, G. A., et al. (2013). Chemical and metabolomic screens identify novel biomarkers and antidotes for cyanide exposure. FASEB J 27, 1928-1938.
24. Siddik, Z. H. (2003). Cisplatin: mode of cytotoxic action and molecular basis of resistance. Oncogene 22, 7265-7279.
25. Smith, R. M., and Martel, A. E. (1976). Critical Stability Constants. In Inorganic Complexes (Plenum Press).
26. Stathopoulos, G. P., Antoniou, D., Dimitroulis, J., Michalopoulou, P., Bastas, A., Marosis, K., Stathopoulos, J., Provata, A., Yiamboudakis, P., Veldekis, D., et al. (2010). Liposomal cisplatin combined with paclitaxel versus cisplatin and paclitaxel in non-small-cell lung cancer: a randomized phase III multicenter trial. Ann Oncol 21, 2227-2232.
27. Strumberg, D., Brugge, S., Korn, M. W., Koeppen, S., Ranft, J., Scheiber, G., Reiners, C., Mockel, C., Seeber, S., and Scheulen, M. E. (2002). Evaluation of long-term toxicity in patients after cisplatin-based chemotherapy for non-seminomatous testicular cancer. *Ann Oncol* 13, 229-236.
28. TOXNET, N. Soduim chloroplatinate. In ChemIDplus.
29. Wisnovsky, S. P., Wilson, J. J., Radford, R. J., Pereira, M. P., Chan, M. R., Laposa, R. R., Lippard, S. J., and Kelley, S. O. (2013). Targeting mitochondrial DNA with a platinum-based anticancer agent. *Chem Biol* 20, 1323-1328.
30. Zhou, W., Wang, X., Hu, M., Zhu, C., and Guo, Z. (2014). A mitochondrion-targeting copper complex exhibits potent cytotoxicity against cisplatin-resistant tumor cells through multiple mechanisms of action. *Chem Sci* 5, 2761-2770.
31. Nogue-Xarau, S., Duenas, A. & Burillo, G. Acute chemical emergencies. *N Engl J Med* 350, 2102-2104, (2004).
32. Sousa, A. B., Manzano, H., Soto-Blanco, B. & Gorniak, S. L. Toxicokinetics of cyanide in rats, pigs and goats after oral dosing with potassium cyanide. *Arch Toxicol* 77, 330-334, (2003).
33. Purser, D. A., Grimshaw, P. & Berrill, K. R. Intoxication by cyanide in fires: a study in monkeys using polyacrylonitrile. *Arch Environ Health* 39, 394-400 (1984).
34. Antonini, E., Brunori, M., Greenwood, C., Malmstrom, B. G. & Rotilio, G. C. The interaction of cyanide with cytochrome oxidase. *Eur J Biochem* 23, 396-400 (1971).
35. Morocco, A. P. Cyanides. *Crit Care Clin* 21, 691-705.
36. Brenner, M. et al. Comparison of cobinamide to hydroxocobalamin in reversing cyanide physiologic effects in rabbits using diffuse optical spectroscopy monitoring. *J Biomed Opt* 15, 017001, (2010).
37. Marraffa, J. M., Cohen, V. & Howland, M. A. Antidotes for toxicological emergencies: a practical review. *Am J Health Syst Pharm* 69, 199-212, (2012).
38. Hall, A. H., Dart, R. & Bogdan, G. Sodium thiosulfate or hydroxocobalamin for the empiric treatment of cyanide poisoning? *Ann Emerg Med* 49, 806-813, (2007).
39. Bebarta, V. S. et al. Intravenous cobinamide versus hydroxocobalamin for acute treatment of severe cyanide poisoning in a swine (*Sus scrofa*) model. *Ann Emerg Med* 64, 612-619, (2014).
40. MacRae, C. A. et al. A countermeasure development pipeline. *Ann NY Acad Sci* 1378, 58-67, (2016).
41. Nath, A. K. et al. Cisplatin Analogs Confer Protection against Cyanide Poisoning. *Cell Chem Biol* 24, 565-575 e564, (2017).
42. Braddock, P. D. et al. Structure and activity relationships of platinum complexes with anti-tumour activity. *Chem Biol Interact* 11, 145-161 (1975).
43. Bolliger, A. P. & Everds, N. in *The Laboratory Mouse* Ch. 2.9, 331-347 (Elsevier, 2012).
44. Bebarta, V. S. et al. Sodium Nitrite and Sodium Thiosulfate Are Effective Against Acute Cyanide Poisoning When Administered by Intramuscular Injection. *Ann Emerg Med* 69, 718-725 e714, (2017).
45. Helke, K. L. & Swindle, M. M. Animal models of toxicology testing: the role of pigs. *Expert Opin Drug Metab Toxicol* 9, 127-139, (2013).
46. Dalgaard, L. Comparison of minipig, dog, monkey and human drug metabolism and disposition. *J Pharmacol Toxicol Methods* 74, 80-92, (2015).
47. Thompson, S. W., Davis, L. E., Kornfeld, M., Hilgers, R. D. & Standefer, J. C. Cisplatin neuropathy. Clinical, electrophysiologic, morphologic, and toxicologic studies. *Cancer* 54, 1269-1275 (1984).
48. Hayes, D. M. et al. High dose cis-platinum diammine dichloride: amelioration of renal toxicity by mannitol diuresis. *Cancer* 39, 1372-1381 (1977).
49. Yao, X., Panichpisal, K., Kurtzman, N. & Nugent, K. Cisplatin nephrotoxicity: a review. *Am J Med Sci* 334, 115-124, (2007).
50. Demchak, P. A. et al. Interleukin-2 and high-dose cisplatin in patients with metastatic melanoma: a pilot study. *J Clin Oncol* 9, 1821-1830, (1991).
51. Lee, J. et al. Noninvasive optical cytochrome c oxidase redox state measurements using diffuse optical spectroscopy. *J Biomed Opt* 19, 055001, (2014).
52. Lee, J., Armstrong, J., Kreuter, K., Tromberg, B. J. & Brenner, M. Non-invasive in vivo diffuse optical spectroscopy monitoring of cyanide poisoning in a rabbit model. *Physiol Meas* 28, 1057-1066, (2007).
53. Kimberly, W. T. et al. Metabolite profiling identifies anandamide as a biomarker of nonalcoholic steatohepatitis. *JCI Insight* 2, (2017).

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:
1. A unit dosage form comprising:
(i) a compound selected from:

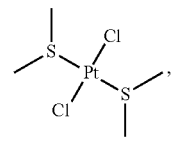

(33)

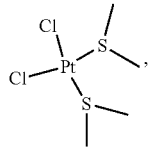

(35)

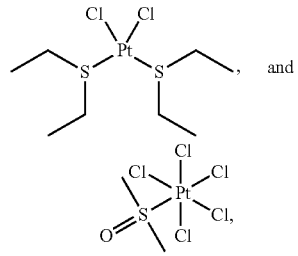

or a pharmaceutically acceptable salt thereof, and
(ii) a pharmaceutically acceptable carrier,
wherein the unit dosage form is in the form of a tablet, capsule, or ampule suitable for direct administration to a subject, and
wherein the unit dosage form comprises a therapeutically effective amount to provide protection against cyanide poisoning.

2. The pharmaceutical composition of claim 1, wherein the compound is:

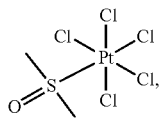

or a pharmaceutically acceptable salt thereof.

3. The pharmaceutical composition of claim 2, wherein the compound is selected from:

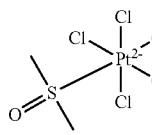 and 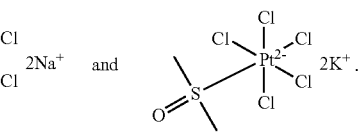

4. The pharmaceutical composition of claim 1, wherein the compound is:

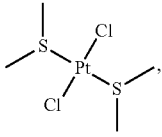

or a pharmaceutically acceptable salt thereof.

5. The pharmaceutical composition of claim 1, wherein the compound is:

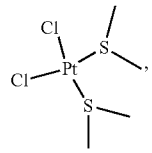

or a pharmaceutically acceptable salt thereof.

6. The pharmaceutical composition of claim 1, wherein the compound is:

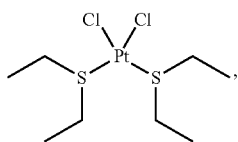

(35)

or a pharmaceutically acceptable salt thereof.

7. The pharmaceutical composition of claim 1, wherein the pharmaceutical composition is suitable for administration by an intramuscular injection.

* * * * *